US008623828B2

(12) United States Patent
Ho et al.

(10) Patent No.: US 8,623,828 B2

(45) Date of Patent: Jan. 7, 2014

(54) BLOCKING MESOTHELIN PEPTIDE FRAGMENTS

(75) Inventors: Mitchell Ho, Bethesda, MD (US); Ira Pastan, Bethesda, MD (US); Osamu Kaneko, Stanford, CA (US); Byungkook Lee, Bethesda, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 224 days.

(21) Appl. No.: 13/133,136

(22) PCT Filed: Dec. 5, 2008

(86) PCT No.: PCT/US2008/085743

§ 371 (c)(1), (2), (4) Date: Jun. 20, 2011

(87) PCT Pub. No.: WO2010/065044

PCT Pub. Date: Jun. 10, 2010

(65) Prior Publication Data

US 2011/0236385 A1 Sep. 29, 2011

(51) Int. Cl.
*C07K 5/00* (2006.01)

(52) U.S. Cl.
USPC .......................................... 514/19.2; 530/324

(58) Field of Classification Search
None
See application file for complete search history.

(56) References Cited

U.S. PATENT DOCUMENTS

| | | | | |
|---|---|---|---|---|
| 6,770,445 | B1 * | 8/2004 | Scholler et al. | 435/7.1 |
| 6,991,901 | B2 * | 1/2006 | Rastelli et al. | 435/6.16 |
| 7,125,663 | B2 * | 10/2006 | Schlegel et al. | 435/6.14 |
| 7,488,813 | B2 * | 2/2009 | Pollock et al. | 536/23.1 |

FOREIGN PATENT DOCUMENTS

WO WO 2008/141044 A2 11/2008

OTHER PUBLICATIONS

Burgess et al, Journal of Cell Biology vol. 111 Nov. 1990 2129-2138.*

Lazar et al Molecular and Cellular Biology Mar. 1988 vol. 8 No. 3 1247-1252.*

Dermer (Bio/Technology, 1994, 12:320).*

Freshney (Culture of Animal Cells, A Manual of Basic Technique, Alan R. Liss, Inc., 1983, New York, p. 4).*

Gura (Science, 1997, 278:1041-1042).*

Jain (Sci. Am., 1994, 271:58-65).*

Haigh et al Oncology vol. 13 p. 1561 (1999).*

Bergan, L., et al., "Development and in vitro validation of anti-mesothelin biobodies that prevent CA125/Mesothelin-dependent cell attachment," *Cancer Letters*, vol. 255(2), pp. 263-274 (Aug. 21, 2007).

Kaneko, O., et al., "A Binding Domain on Mesothelin for CA125/MUC16," *The Journal of Biological Chemistry*, vol. 284(6), pp. 3739-3749 (Feb. 6, 2009).

Möbus, V., et al., "Immune responses to murine monoclonal anti-body-B43.13 correlate with prolonged survival of women with recurrent ovarian cancer," *American Journal of Obstetrics and Gynecology*, vol. 189(1), pp. 28-36 (Jul. 1, 2003).

Rump, A., et al., "Binding of Ovarian Cancer Antigen CA125/MUC16 to Mesothelin Mediates Cell Adhesion," *The Journal of Biological Chemistry*, vol. 279(10), pp. 9190-9198 (Mar. 5, 2004).

Scholler, N., et al., "Development of a CA125-mesothelin cell adhesion assay as a screening tool for biologics discovery," *Cancer Letters*, vol. 247(1), pp. 130-136 (Dec. 22, 2006).

Database UniProt [Online], "SubName: Full=MSLN protein;," retrieved from EBI, Accession No. A6QP39, 1pg (Aug. 21, 2007).

* cited by examiner

*Primary Examiner* — Sheela J Huff

(74) *Attorney, Agent, or Firm* — Kilpatrick Townsend & Stockton LLP

(57) ABSTRACT

The present invention provides mesothelin peptide fragments corresponding to the CA125 binding site of mesothelin. The peptide fragments find use in disrupting the binding interaction between mesothelin and CA 125, for example, in the treatment and prevention of cancers that require the interaction of mesothelin and CA125 for growth, progression and/or metastasis.

27 Claims, 10 Drawing Sheets

A

B

A

B

CA125-Binding Domain on Mesothelin

SEQUENCE LISTING

```
<160> NUMBER OF SEQ ID NOS: 42

<210> SEQ ID NO 1
<211> LENGTH: 630
<212> TYPE: PRT
<213> ORGANISM: Homo sapiens
<220> FEATURE:
<223> OTHER INFORMATION: human mesothelin (MSLN, hnMSLN)
```

-continued

<400> SEQUENCE: 1

```
Met Ala Leu Pro Thr Ala Arg Pro Leu Leu Gly Ser Cys Gly Thr Pro
 1               5                  10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415
```

-continued

```
Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630


<210> SEQ ID NO 2
<211> LENGTH: 64
<212> TYPE: PRT
<213> ORGANISM: Artificial Sequence
<220> FEATURE:
<223> OTHER INFORMATION: human mesothelin fragment residues 296-359,
      Region IAB
<220> FEATURE:
<221> NAME/KEY: VARIANT
<222> LOCATION: (26)...(59)
<223> OTHER INFORMATION: Xaa = any amino acid

<400> SEQUENCE: 2

Glu Val Glu Lys Thr Ala Cys Pro Ser Gly Lys Lys Ala Arg Glu Ile
 1               5                  10                  15

Asp Glu Ser Leu Ile Phe Tyr Lys Lys Xaa Glu Leu Xaa Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys Xaa Lys Leu Asp Glu Leu
    50                  55                  60


<210> SEQ ID NO 3
<211> LENGTH: 64
<212> TYPE: PRT
<213> ORGANISM: Artificial Sequence
<220> FEATURE:
<223> OTHER INFORMATION: human mesothelin fragment residues 296-359,
      Region IAB

<400> SEQUENCE: 3
```

-continued

Glu Val Glu Lys Thr Ala Cys Pro Ser Gly Lys Lys Ala Arg Glu Ile
1 5 10 15

Asp Glu Ser Leu Ile Phe Tyr Lys Lys Trp Glu Leu Glu Ala Cys Val
20 25 30

Asp Ala Ala Leu Leu Ala Thr Gln Met Asp Arg Val Asn Ala Ile Pro
35 40 45

Phe Thr Tyr Glu Gln Leu Asp Val Leu Lys His Lys Leu Asp Glu Leu
50 55 60

<210> SEQ ID NO 4
<211> LENGTH: 95
<212> TYPE: PRT
<213> ORGANISM: Artificial Sequence
<220> FEATURE:
<223> OTHER INFORMATION: human mesothelin fragment residues 296-390, Region I
<220> FEATURE:
<221> NAME/KEY: VARIANT
<222> LOCATION: (26)...(59)
<223> OTHER INFORMATION: Xaa = any amino acid

<400> SEQUENCE: 4

Glu Val Glu Lys Thr Ala Cys Pro Ser Gly Lys Lys Ala Arg Glu Ile
1 5 10 15

Asp Glu Ser Leu Ile Phe Tyr Lys Lys Xaa Glu Leu Xaa Ala Cys Val
20 25 30

Asp Ala Ala Leu Leu Ala Thr Gln Met Asp Arg Val Asn Ala Ile Pro
35 40 45

Phe Thr Tyr Glu Gln Leu Asp Val Leu Lys Xaa Lys Leu Asp Glu Leu
50 55 60

Tyr Pro Gln Gly Tyr Pro Glu Ser Val Ile Gln His Leu Gly Tyr Leu
65 70 75 80

Phe Leu Lys Met Ser Pro Glu Asp Ile Arg Lys Trp Asn Val Thr
85 90 95

<210> SEQ ID NO 5
<211> LENGTH: 95
<212> TYPE: PRT
<213> ORGANISM: Artificial Sequence
<220> FEATURE:
<223> OTHER INFORMATION: human mesothelin fragment residues 296-390, Region I

<400> SEQUENCE: 5

Glu Val Glu Lys Thr Ala Cys Pro Ser Gly Lys Lys Ala Arg Glu Ile
1 5 10 15

Asp Glu Ser Leu Ile Phe Tyr Lys Lys Trp Glu Leu Glu Ala Cys Val
20 25 30

Asp Ala Ala Leu Leu Ala Thr Gln Met Asp Arg Val Asn Ala Ile Pro
35 40 45

Phe Thr Tyr Glu Gln Leu Asp Val Leu Lys His Lys Leu Asp Glu Leu
50 55 60

Tyr Pro Gln Gly Tyr Pro Glu Ser Val Ile Gln His Leu Gly Tyr Leu
65 70 75 80

Phe Leu Lys Met Ser Pro Glu Asp Ile Arg Lys Trp Asn Val Thr
85 90 95

<210> SEQ ID NO 6
<211> LENGTH: 6
<212> TYPE: PRT
<213> ORGANISM: Artificial Sequence
<220> FEATURE:
<223> OTHER INFORMATION: 6xHis tag, His tag

<400> SEQUENCE: 6

His His His His His His
1 5

<210> SEQ ID NO 7
<211> LENGTH: 327
<212> TYPE: PRT
<213> ORGANISM: Artificial Sequence
<220> FEATURE:
<223> OTHER INFORMATION: human mesothelin fragment starting at Region I

<400> SEQUENCE: 7

Glu Val Glu Lys Thr Ala Cys Pro Ser Gly Lys Lys Ala Arg Glu Ile
1 5 10 15

Asp Glu Ser Leu Ile Phe Tyr Lys Lys Trp Glu Leu Glu Ala Cys Val
20 25 30

Asp Ala Ala Leu Leu Ala Thr Gln Met Asp Arg Val Asn Ala Ile Pro
35 40 45

Phe Thr Tyr Glu Gln Leu Asp Val Leu Lys His Lys Leu Asp Glu Leu
50 55 60

Tyr Pro Gln Gly Tyr Pro Glu Ser Val Ile Gln His Leu Gly Tyr Leu
65 70 75 80

Phe Leu Lys Met Ser Pro Glu Asp Ile Arg Lys Trp Asn Val Thr Ser
85 90 95

Leu Glu Thr Leu Lys Ala Leu Leu Glu Val Asn Lys Gly His Glu Met
100 105 110

Ser Pro Gln Val Ala Thr Leu Ile Asp Arg Phe Val Lys Gly Arg Gly
115 120 125

Gln Leu Asp Lys Asp Thr Leu Asp Thr Leu Thr Ala Phe Tyr Pro Gly
130 135 140

Tyr Leu Cys Ser Leu Ser Pro Glu Glu Leu Ser Ser Val Pro Pro Ser
145 150 155 160

Ser Ile Trp Ala Val Arg Pro Gln Asp Leu Asp Thr Cys Asp Pro Arg
165 170 175

Gln Leu Asp Val Leu Tyr Pro Lys Ala Arg Leu Ala Phe Gln Asn Met
180 185 190

Asn Gly Ser Glu Tyr Phe Val Lys Ile Gln Ser Phe Leu Gly Gly Ala
195 200 205

Pro Thr Glu Asp Leu Lys Ala Leu Ser Gln Gln Asn Val Ser Met Asp
210 215 220

Leu Ala Thr Phe Met Lys Leu Arg Thr Asp Ala Val Leu Pro Leu Thr
225 230 235 240

Val Ala Glu Val Gln Lys Leu Leu Gly Pro His Val Glu Gly Leu Lys
245 250 255

Ala Glu Glu Arg His Arg Pro Val Arg Asp Trp Ile Leu Arg Gln Arg
260 265 270

Gln Asp Asp Leu Asp Thr Leu Gly Leu Gly Leu Gln Gly Gly Ile Pro
275 280 285

Asn Gly Tyr Leu Val Leu Asp Leu Ser Val Gln Glu Ala Leu Ser Gly
290 295 300

Thr Pro Cys Leu Leu Gly Pro Gly Pro Val Leu Thr Val Leu Ala Leu
305 310 315 320

Leu Leu Ala Ser Thr Leu Ala
325

<210> SEQ ID NO 8
<211> LENGTH: 328
<212> TYPE: PRT
<213> ORGANISM: Artificial Sequence
<220> FEATURE:
<223> OTHER INFORMATION: mouse mesothelin fragment starting at Region I

<400> SEQUENCE: 8

```
Asp Ala Glu Gln Lys Ala Cys Pro Pro Gly Lys Glu Pro Tyr Lys Val
 1               5                  10                  15

Asp Glu Asp Leu Ile Phe Tyr Gln Asn Trp Glu Leu Glu Ala Cys Val
            20                  25                  30

Asp Gly Thr Met Leu Ala Arg Gln Met Asp Leu Val Asn Glu Ile Pro
        35                  40                  45

Phe Thr Tyr Glu Gln Leu Ser Ile Phe Lys His Lys Leu Asp Lys Thr
    50                  55                  60

Tyr Pro Gln Gly Tyr Pro Glu Ser Leu Ile Gln Gln Leu Gly His Phe
65                  70                  75                  80

Phe Arg Tyr Val Ser Pro Glu Asp Ile His Gln Trp Asn Val Thr Ser
                85                  90                  95

Pro Asp Thr Val Lys Thr Leu Leu Lys Val Ser Lys Gly Gln Lys Met
            100                 105                 110

Asn Ala Gln Ala Ile Ala Leu Val Ala Cys Tyr Leu Arg Gly Gly Gly
        115                 120                 125

Gln Leu Asp Glu Asp Met Val Lys Ala Leu Gly Asp Ile Pro Leu Ser
    130                 135                 140

Tyr Leu Cys Asp Phe Ser Pro Gln Asp Leu His Ser Val Pro Ser Ser
145                 150                 155                 160

Val Met Trp Leu Val Gly Pro Gln Asp Leu Asp Lys Cys Ser Gln Arg
                165                 170                 175

His Leu Gly Leu Leu Tyr Gln Lys Ala Cys Ser Ala Phe Gln Asn Val
            180                 185                 190

Ser Gly Leu Glu Tyr Phe Glu Lys Ile Lys Thr Phe Leu Gly Gly Ala
        195                 200                 205

Ser Val Lys Asp Leu Arg Ala Leu Ser Gln His Asn Val Ser Met Asp
    210                 215                 220

Ile Ala Thr Phe Lys Arg Leu Gln Val Asp Ser Leu Val Gly Leu Ser
225                 230                 235                 240

Val Ala Glu Val Gln Lys Leu Leu Gly Pro Asn Ile Val Asp Leu Lys
                245                 250                 255

Thr Glu Glu Asp Lys Ser Pro Val Arg Asp Trp Leu Phe Arg Gln His
            260                 265                 270

Gln Lys Asp Leu Asp Arg Leu Gly Leu Gly Leu Gln Gly Gly Ile Pro
        275                 280                 285

Asn Gly Tyr Leu Val Leu Asp Phe Asn Val Arg Glu Ala Phe Ser Ser
    290                 295                 300

Arg Ala Ser Leu Leu Gly Pro Gly Phe Val Leu Ile Trp Ile Pro Ala
305                 310                 315                 320

Leu Leu Pro Ala Leu Arg Leu Ser
                325
```

<210> SEQ ID NO 9
<211> LENGTH: 328
<212> TYPE: PRT
<213> ORGANISM: Artificial Sequence
<220> FEATURE:

<223> OTHER INFORMATION: consensus sequence of human and mouse
mesothelin fragment starting at Region I
<220> FEATURE:
<221> NAME/KEY: VARIANT
<222> LOCATION: (2)...(2)
<223> OTHER INFORMATION: Xaa = Val or Ala
<220> FEATURE:
<221> NAME/KEY: VARIANT
<222> LOCATION: (4)...(4)
<223> OTHER INFORMATION: Xaa = Lys or Gln
<220> FEATURE:
<221> NAME/KEY: VARIANT
<222> LOCATION: (5)...(5)
<223> OTHER INFORMATION: Xaa = Thr or Lys
<220> FEATURE:
<221> NAME/KEY: VARIANT
<222> LOCATION: (9)...(9)
<223> OTHER INFORMATION: Xaa = Ser or Pro
<220> FEATURE:
<221> NAME/KEY: VARIANT
<222> LOCATION: (12)...(12)
<223> OTHER INFORMATION: Xaa = Lys or Gln
<220> FEATURE:
<221> NAME/KEY: VARIANT
<222> LOCATION: (13)...(13)
<223> OTHER INFORMATION: Xaa = Ala or Pro
<220> FEATURE:
<221> NAME/KEY: VARIANT
<222> LOCATION: (14)...(14)
<223> OTHER INFORMATION: Xaa = Arg or Tyr
<220> FEATURE:
<221> NAME/KEY: VARIANT
<222> LOCATION: (15)...(15)
<223> OTHER INFORMATION: Xaa = Glu or Lys
<220> FEATURE:
<221> NAME/KEY: VARIANT
<222> LOCATION: (19)...(19)
<223> OTHER INFORMATION: Xaa = Ser or Asp
<220> FEATURE:
<221> NAME/KEY: VARIANT
<222> LOCATION: (24)...(24)
<223> OTHER INFORMATION: Xaa = Lys or Gln
<220> FEATURE:
<221> NAME/KEY: VARIANT
<222> LOCATION: (25)...(25)
<223> OTHER INFORMATION: Xaa = Lys or Asn
<220> FEATURE:
<221> NAME/KEY: VARIANT
<222> LOCATION: (35)...(35)
<223> OTHER INFORMATION: Xaa = Ala or Thr
<220> FEATURE:
<221> NAME/KEY: VARIANT
<222> LOCATION: (39)...(39)
<223> OTHER INFORMATION: Xaa = Thr or Arg
<220> FEATURE:
<221> NAME/KEY: VARIANT
<222> LOCATION: (43)...(43)
<223> OTHER INFORMATION: Xaa = Arg or Leu
<220> FEATURE:
<221> NAME/KEY: VARIANT
<222> LOCATION: (46)...(46)
<223> OTHER INFORMATION: Xaa = Ala or Glu
<220> FEATURE:
<221> NAME/KEY: VARIANT
<222> LOCATION: (55)...(55)
<223> OTHER INFORMATION: Xaa = Asp or Ser
<220> FEATURE:
<221> NAME/KEY: VARIANT
<222> LOCATION: (57)...(57)
<223> OTHER INFORMATION: Xaa = Leu or Phe
<220> FEATURE:
<221> NAME/KEY: VARIANT
<222> LOCATION: (57)...(57)
<223> OTHER INFORMATION: Xaa = Leu or Phe
<220> FEATURE:
<221> NAME/KEY: VARIANT
<222> LOCATION: (63)...(63)
<223> OTHER INFORMATION: Xaa = Glu or Lys
<220> FEATURE:
<221> NAME/KEY: VARIANT
<222> LOCATION: (64)...(64)
<223> OTHER INFORMATION: Xaa = Leu or Thr
<220> FEATURE:
<221> NAME/KEY: VARIANT
<222> LOCATION: (76)...(76)
<223> OTHER INFORMATION: Xaa = His or Gln
<220> FEATURE:
<221> NAME/KEY: VARIANT
<222> LOCATION: (79)...(79)
<223> OTHER INFORMATION: Xaa = Tyr or His
<220> FEATURE:
<221> NAME/KEY: VARIANT
<222> LOCATION: (80)...(80)
<223> OTHER INFORMATION: Xaa = Leu or Phe
<220> FEATURE:
<221> NAME/KEY: VARIANT
<222> LOCATION: (82)...(82)
<223> OTHER INFORMATION: Xaa = Leu or Arg
<220> FEATURE:
<221> NAME/KEY: VARIANT
<222> LOCATION: (83)...(83)
<223> OTHER INFORMATION: Xaa = Lys or Tyr
<220> FEATURE:
<221> NAME/KEY: VARIANT
<222> LOCATION: (90)...(90)
<223> OTHER INFORMATION: Xaa = Arg or His
<220> FEATURE:
<221> NAME/KEY: VARIANT
<222> LOCATION: (91)...(91)
<223> OTHER INFORMATION: Xaa = Lys or Gln
<220> FEATURE:
<221> NAME/KEY: VARIANT
<222> LOCATION: (97)...(97)
<223> OTHER INFORMATION: Xaa = Leu or Pro
<220> FEATURE:
<221> NAME/KEY: VARIANT
<222> LOCATION: (102)...(102)
<223> OTHER INFORMATION: Xaa = Ala or Thr
<220> FEATURE:
<221> NAME/KEY: VARIANT
<222> LOCATION: (105)...(105)
<223> OTHER INFORMATION: Xaa = Glu or Lys
<220> FEATURE:
<221> NAME/KEY: VARIANT
<222> LOCATION: (107)...(107)
<223> OTHER INFORMATION: Xaa = Asn or Ser
<220> FEATURE:
<221> NAME/KEY: VARIANT
<222> LOCATION: (110)...(110)
<223> OTHER INFORMATION: Xaa = His or Gln
<220> FEATURE:
<221> NAME/KEY: VARIANT
<222> LOCATION: (111)...(111)
<223> OTHER INFORMATION: Xaa = Glu or Lys
<220> FEATURE:
<221> NAME/KEY: VARIANT
<222> LOCATION: (113)...(113)
<223> OTHER INFORMATION: Xaa = Ser or Asn
<220> FEATURE:
<221> NAME/KEY: VARIANT
<222> LOCATION: (114)...(114)
<223> OTHER INFORMATION: Xaa = Pro or Ala
<220> FEATURE:
<221> NAME/KEY: VARIANT
<222> LOCATION: (116)...(116)
<223> OTHER INFORMATION: Xaa = Val or Ala
<220> FEATURE:
<221> NAME/KEY: VARIANT
<222> LOCATION: (117)...(117)
<223> OTHER INFORMATION: Xaa = Ala or Ile
<220> FEATURE:
<221> NAME/KEY: VARIANT
<222> LOCATION: (118)...(118)
<223> OTHER INFORMATION: Xaa = Thr or Ala
<220> FEATURE:
<221> NAME/KEY: VARIANT
<222> LOCATION: (121)...(121)
<223> OTHER INFORMATION: Xaa = Asp or Ala
<220> FEATURE:
<221> NAME/KEY: VARIANT
<222> LOCATION: (122)...(122)
<223> OTHER INFORMATION: Xaa = Arg or Cys
<220> FEATURE:
<221> NAME/KEY: VARIANT
<222> LOCATION: (127)...(127)
<223> OTHER INFORMATION: Xaa = Arg or Gly
<220> FEATURE:
<221> NAME/KEY: VARIANT
<222> LOCATION: (132)...(132)
<223> OTHER INFORMATION: Xaa = Lys or Glu
<220> FEATURE:
<221> NAME/KEY: VARIANT
<222> LOCATION: (134)...(134)
<223> OTHER INFORMATION: Xaa = Thr or Met
<220> FEATURE:
<221> NAME/KEY: VARIANT
<222> LOCATION: (136)...(136)
<223> OTHER INFORMATION: Xaa = Asp or Lys
<220> FEATURE:
<221> NAME/KEY: VARIANT
<222> LOCATION: (137)...(137)
<223> OTHER INFORMATION: Xaa = Thr or Ala
<220> FEATURE:
<221> NAME/KEY: VARIANT
<222> LOCATION: (139)...(139)
<223> OTHER INFORMATION: Xaa = Thr or Gly
<220> FEATURE:
<221> NAME/KEY: VARIANT
<222> LOCATION: (140)...(140)
<223> OTHER INFORMATION: Xaa = Ala or Asp
<220> FEATURE:
<221> NAME/KEY: VARIANT
<222> LOCATION: (140)...(140)
<223> OTHER INFORMATION: Xaa = Ala or Asp
<220> FEATURE:
<221> NAME/KEY: VARIANT
<222> LOCATION: (141)...(141)
<223> OTHER INFORMATION: Xaa = Phe or Ile
<220> FEATURE:
<221> NAME/KEY: VARIANT
<222> LOCATION: (142)...(142)
<223> OTHER INFORMATION: Xaa = Tyr or Pro
<220> FEATURE:
<221> NAME/KEY: VARIANT
<222> LOCATION: (143)...(143)
<223> OTHER INFORMATION: Xaa = Pro or Leu
<220> FEATURE:
<221> NAME/KEY: VARIANT
<222> LOCATION: (144)...(144)
<223> OTHER INFORMATION: Xaa = Gly or Ser
<220> FEATURE:
<221> NAME/KEY: VARIANT
<222> LOCATION: (148)...(148)
<223> OTHER INFORMATION: Xaa = Ser or Asp
<220> FEATURE:
<221> NAME/KEY: VARIANT
<222> LOCATION: (149)...(149)
<223> OTHER INFORMATION: Xaa = Leu or Phe
<220> FEATURE:
<221> NAME/KEY: VARIANT
<222> LOCATION: (155)...(155)
<223> OTHER INFORMATION: Xaa = Ser or His
<220> FEATURE:
<221> NAME/KEY: VARIANT
<222> LOCATION: (159)...(159)
<223> OTHER INFORMATION: Xaa = Pro or Ser
<220> FEATURE:
<221> NAME/KEY: VARIANT
<222> LOCATION: (161)...(161)
<223> OTHER INFORMATION: Xaa = Ser or Val
<220> FEATURE:
<221> NAME/KEY: VARIANT
<222> LOCATION: (164)...(164)
<223> OTHER INFORMATION: Xaa = Ala or Leu
<220> FEATURE:
<221> NAME/KEY: VARIANT
<222> LOCATION: (166)...(166)
<223> OTHER INFORMATION: Xaa = Arg or Gly
<220> FEATURE:
<221> NAME/KEY: VARIANT
<222> LOCATION: (172)...(172)
<223> OTHER INFORMATION: Xaa = Thr or Lys
<220> FEATURE:
<221> NAME/KEY: VARIANT
<222> LOCATION: (174)...(174)
<223> OTHER INFORMATION: Xaa = Asp or Ser
<220> FEATURE:
<221> NAME/KEY: VARIANT
<222> LOCATION: (175)...(175)
<223> OTHER INFORMATION: Xaa = Pro or Gln
<220> FEATURE:
<221> NAME/KEY: VARIANT
<222> LOCATION: (177)...(177)
<223> OTHER INFORMATION: Xaa = Gln or His
<220> FEATURE:
<221> NAME/KEY: VARIANT
<222> LOCATION: (179)...(179)
<223> OTHER INFORMATION: Xaa = Asp or Gly
<220> FEATURE:
<221> NAME/KEY: VARIANT
<222> LOCATION: (183)...(183)
<223> OTHER INFORMATION: Xaa = Pro or Gln
<220> FEATURE:
<221> NAME/KEY: VARIANT
<222> LOCATION: (186)...(186)
<223> OTHER INFORMATION: Xaa = Arg or Cys
<220> FEATURE:
<221> NAME/KEY: VARIANT
<222> LOCATION: (187)...(187)
<223> OTHER INFORMATION: Xaa = Leu or Ser
<220> FEATURE:
<221> NAME/KEY: VARIANT
<222> LOCATION: (193)...(193)
<223> OTHER INFORMATION: Xaa = Asn or Ser
<220> FEATURE:
<221> NAME/KEY: VARIANT
<222> LOCATION: (195)...(195)
<223> OTHER INFORMATION: Xaa = Ser or Leu
<220> FEATURE:
<221> NAME/KEY: VARIANT
<222> LOCATION: (199)...(199)
<223> OTHER INFORMATION: Xaa = Val or Glu
<220> FEATURE:
<221> NAME/KEY: VARIANT
<222> LOCATION: (202)...(202)
<223> OTHER INFORMATION: Xaa = Gln or Lys
<220> FEATURE:
<221> NAME/KEY: VARIANT
<222> LOCATION: (209)...(209)
<223> OTHER INFORMATION: Xaa = Pro or Ser
<220> FEATURE:
<221> NAME/KEY: VARIANT
<222> LOCATION: (210)...(210)
<223> OTHER INFORMATION: Xaa = Thr or Val
<220> FEATURE:
<221> NAME/KEY: VARIANT
<222> LOCATION: (211)...(211)
<223> OTHER INFORMATION: Xaa = Glu or Lys
<220> FEATURE:
<221> NAME/KEY: VARIANT
<222> LOCATION: (219)...(219)
<223> OTHER INFORMATION: Xaa = Gln or His
<220> FEATURE:
<221> NAME/KEY: VARIANT
<222> LOCATION: (229)...(229)
<223> OTHER INFORMATION: Xaa = Met or Lys
<220> FEATURE:
<221> NAME/KEY: VARIANT
<222> LOCATION: (232)...(232)
<223> OTHER INFORMATION: Xaa = Arg or Gln
<220> FEATURE:
<221> NAME/KEY: VARIANT
<222> LOCATION: (233)...(233)
<223> OTHER INFORMATION: Xaa = Thr or Val
<220> FEATURE:
<221> NAME/KEY: VARIANT
<222> LOCATION: (235)...(235)
<223> OTHER INFORMATION: Xaa = Ala or Ser
<220> FEATURE:
<221> NAME/KEY: VARIANT
<222> LOCATION: (238)...(238)
<223> OTHER INFORMATION: Xaa = Pro or Gly
<220> FEATURE:
<221> NAME/KEY: VARIANT
<222> LOCATION: (251)...(251)
<223> OTHER INFORMATION: Xaa = His or Asn
<220> FEATURE:
<221> NAME/KEY: VARIANT
<222> LOCATION: (253)...(253)
<223> OTHER INFORMATION: Xaa = Gln or Val
<220> FEATURE:
<221> NAME/KEY: VARIANT
<222> LOCATION: (254)...(254)
<223> OTHER INFORMATION: Xaa = Gly or Asp
<220> FEATURE:
<221> NAME/KEY: VARIANT
<222> LOCATION: (257)...(257)
<223> OTHER INFORMATION: Xaa = Ala or Thr
<220> FEATURE:
<221> NAME/KEY: VARIANT
<222> LOCATION: (260)...(260)
<223> OTHER INFORMATION: Xaa = Arg or Asp
<220> FEATURE:
<221> NAME/KEY: VARIANT
<222> LOCATION: (261)...(261)
<223> OTHER INFORMATION: Xaa = His or Lys
<220> FEATURE:
<221> NAME/KEY: VARIANT
<222> LOCATION: (262)...(262)
<223> OTHER INFORMATION: Xaa = Arg or Ser
<220> FEATURE:
<221> NAME/KEY: VARIANT
<222> LOCATION: (269)...(269)
<223> OTHER INFORMATION: Xaa = Leu or Phe
<220> FEATURE:
<221> NAME/KEY: VARIANT
<222> LOCATION: (272)...(272)
<223> OTHER INFORMATION: Xaa = Arg or His
<220> FEATURE:
<221> NAME/KEY: VARIANT
<222> LOCATION: (274)...(274)
<223> OTHER INFORMATION: Xaa = Asp or Lys
<220> FEATURE:
<221> NAME/KEY: VARIANT
<222> LOCATION: (278)...(278)
<223> OTHER INFORMATION: Xaa = Thr or Arg
<220> FEATURE:
<221> NAME/KEY: VARIANT
<222> LOCATION: (296)...(296)
<223> OTHER INFORMATION: Xaa = Leu or Phe
<220> FEATURE:
<221> NAME/KEY: VARIANT
<222> LOCATION: (297)...(297)
<223> OTHER INFORMATION: Xaa = Ser or Asn
<220> FEATURE:
<221> NAME/KEY: VARIANT
<222> LOCATION: (299)...(299)
<223> OTHER INFORMATION: Xaa = Gln or Arg
<220> FEATURE:
<221> NAME/KEY: VARIANT
<222> LOCATION: (302)...(302)
<223> OTHER INFORMATION: Xaa = Leu or Phe
<220> FEATURE:
<221> NAME/KEY: VARIANT
<222> LOCATION: (304)...(304)
<223> OTHER INFORMATION: Xaa = Gly or Ser
<220> FEATURE:
<221> NAME/KEY: VARIANT
<222> LOCATION: (305)...(305)
<223> OTHER INFORMATION: Xaa = Thr or Arg
<220> FEATURE:
<221> NAME/KEY: VARIANT
<222> LOCATION: (306)...(306)
<223> OTHER INFORMATION: Xaa = Pro or Ala
<220> FEATURE:
<221> NAME/KEY: VARIANT
<222> LOCATION: (307)...(307)
<223> OTHER INFORMATION: Xaa = Cys or Ser
<220> FEATURE:
<221> NAME/KEY: VARIANT

```
<222> LOCATION: (313)...(313)
<223> OTHER INFORMATION: Xaa = Pro or Phe
<220> FEATURE:
<221> NAME/KEY: VARIANT
<222> LOCATION: (316)...(316)
<223> OTHER INFORMATION: Xaa = Thr or Ile
<220> FEATURE:
<221> NAME/KEY: VARIANT
<222> LOCATION: (319)...(319)
<223> OTHER INFORMATION: Xaa = Leu or Pro
<220> FEATURE:
<221> NAME/KEY: VARIANT
<222> LOCATION: (323)...(323)
<223> OTHER INFORMATION: Xaa = Leu or Pro
<220> FEATURE:
<221> NAME/KEY: VARIANT
<222> LOCATION: (325)...(325)
<223> OTHER INFORMATION: Xaa = Ser or Leu
<220> FEATURE:
<221> NAME/KEY: VARIANT
<222> LOCATION: (326)...(326)
<223> OTHER INFORMATION: Xaa = Thr or Arg
<220> FEATURE:
<221> NAME/KEY: VARIANT
<222> LOCATION: (328)...(328)
<223> OTHER INFORMATION: Xaa = Ala or Ser

<400> SEQUENCE: 9

Glu Xaa Glu Xaa Xaa Ala Cys Pro Xaa Gly Lys Xaa Xaa Xaa Xaa Ile
 1               5                  10                  15

Asp Glu Xaa Leu Ile Phe Tyr Xaa Xaa Trp Glu Leu Glu Ala Cys Val
            20                  25                  30

Asp Ala Xaa Leu Leu Ala Xaa Gln Met Asp Xaa Val Asn Xaa Ile Pro
        35                  40                  45

Phe Thr Tyr Glu Gln Leu Xaa Val Xaa Lys His Lys Leu Asp Xaa Xaa
    50                  55                  60

Tyr Pro Gln Gly Tyr Pro Glu Ser Val Ile Gln Xaa Leu Gly Xaa Xaa
65                  70                  75                  80

Phe Xaa Xaa Met Ser Pro Glu Asp Ile Xaa Xaa Trp Asn Val Thr Ser
                85                  90                  95

Xaa Glu Thr Leu Lys Xaa Leu Leu Xaa Val Xaa Lys Gly Xaa Xaa Met
            100                 105                 110

Xaa Xaa Gln Xaa Xaa Xaa Leu Ile Xaa Xaa Phe Val Lys Gly Xaa Gly
        115                 120                 125

Gln Leu Asp Xaa Asp Xaa Leu Xaa Xaa Leu Xaa Xaa Xaa Xaa Xaa Xaa
    130                 135                 140

Tyr Leu Cys Xaa Xaa Ser Pro Glx Glu Leu Xaa Ser Val Pro Xaa Ser
145                 150                 155                 160

Xaa Ile Trp Xaa Val Xaa Pro Gln Asp Leu Asp Xaa Cys Xaa Xaa Arg
                165                 170                 175

Xaa Leu Xaa Val Leu Tyr Xaa Lys Ala Xaa Xaa Ala Phe Gln Asn Met
            180                 185                 190

Xaa Gly Xaa Glu Tyr Phe Xaa Lys Ile Xaa Ser Phe Leu Gly Gly Ala
        195                 200                 205

Xaa Xaa Xaa Asp Leu Lys Ala Leu Ser Gln Xaa Asn Val Ser Met Asp
    210                 215                 220

Leu Ala Thr Phe Xaa Lys Leu Xaa Xaa Asp Xaa Val Leu Xaa Leu Thr
225                 230                 235                 240

Val Ala Glu Val Gln Lys Leu Leu Gly Pro Xaa Val Xaa Xaa Leu Lys
                245                 250                 255

Xaa Glu Glu Xaa Xaa Xaa Pro Val Arg Asp Trp Ile Xaa Arg Gln Xaa
            260                 265                 270
```

-continued

```
Gln Xaa Asp Leu Asp Xaa Leu Gly Leu Gly Leu Gln Gly Gly Ile Pro
        275                 280                 285

Asn Gly Tyr Leu Val Leu Asp Xaa Xaa Val Xaa Glu Ala Xaa Ser Xaa
    290                 295                 300

Xaa Xaa Xaa Leu Leu Gly Pro Gly Xaa Val Leu Xaa Trp Val Xaa Ala
305                 310                 315                 320

Leu Leu Xaa Ala Xaa Xaa Leu Xaa
                325


<210> SEQ ID NO 10
<211> LENGTH: 13
<212> TYPE: PRT
<213> ORGANISM: Artificial Sequence
<220> FEATURE:
<223> OTHER INFORMATION: artificial T-cell epitope, MHC Class II pan DR
      epitope, PADRE peptide
<220> FEATURE:
<221> NAME/KEY: VARIANT
<222> LOCATION: (3)...(3)
<223> OTHER INFORMATION: Xaa = cyclohexylalanine, Tyr or Phe

<400> SEQUENCE: 10

Ala Lys Xaa Val Ala Ala Trp Thr Leu Lys Ala Ala Ala
 1               5                  10


<210> SEQ ID NO 11
<211> LENGTH: 36
<212> TYPE: DNA
<213> ORGANISM: Artificial Sequence
<220> FEATURE:
<223> OTHER INFORMATION: Region I (296-390) fragment forward primer
      used to construct truncated mesothelin mutant

<400> SEQUENCE: 11

agaagaagag aattcgaagt ggagaagaca gcctgt                               36


<210> SEQ ID NO 12
<211> LENGTH: 39
<212> TYPE: DNA
<213> ORGANISM: Artificial Sequence
<220> FEATURE:
<223> OTHER INFORMATION: Region I (296-390) fragment reverse primer
      used to construct truncated mesothelin mutant

<400> SEQUENCE: 12

ctcttcttct gcggccgccg tcacattcca cttgcgaat                            39


<210> SEQ ID NO 13
<211> LENGTH: 36
<212> TYPE: DNA
<213> ORGANISM: Artificial Sequence
<220> FEATURE:
<223> OTHER INFORMATION: Region II (391-486) fragment forward primer
      used to construct truncated mesothelin mutant

<400> SEQUENCE: 13

agaagaagag aattctccct ggagaccctg aaggct                               36


<210> SEQ ID NO 14
<211> LENGTH: 39
<212> TYPE: DNA
<213> ORGANISM: Artificial Sequence
<220> FEATURE:
<223> OTHER INFORMATION: Region II (391-486) fragment reverse primer
      used to construct truncated mesothelin mutant

<400> SEQUENCE: 14
```

ctcttcttct gcggccgcct ggaaagcaag gcgggcctt 39

<210> SEQ ID NO 15
<211> LENGTH: 36
<212> TYPE: DNA
<213> ORGANISM: Artificial Sequence
<220> FEATURE:
<223> OTHER INFORMATION: Region III (487-581) fragment forward primer used to construct truncated mesothelin mutant

<400> SEQUENCE: 15
agaagaagag aattcaacat gaacgggtcc gaatac 36

<210> SEQ ID NO 16
<211> LENGTH: 39
<212> TYPE: DNA
<213> ORGANISM: Artificial Sequence
<220> FEATURE:
<223> OTHER INFORMATION: Region III (487-581) fragment reverse primer used to construct truncated mesothelin mutant

<400> SEQUENCE: 16
ctcttcttct gcggccgcgc cctgtagccc cagccccag 39

<210> SEQ ID NO 17
<211> LENGTH: 36
<212> TYPE: DNA
<213> ORGANISM: Artificial Sequence
<220> FEATURE:
<223> OTHER INFORMATION: Region IAB (296-359) fragment forward primer used to construct truncated mesothelin mutant

<400> SEQUENCE: 17
agaagaagag aattcgaagt ggagaagaca gcctgt 36

<210> SEQ ID NO 18
<211> LENGTH: 39
<212> TYPE: DNA
<213> ORGANISM: Artificial Sequence
<220> FEATURE:
<223> OTHER INFORMATION: Region IAB (296-359) fragment reverse primer used to construct truncated mesothelin mutant

<400> SEQUENCE: 18
ctcttcttct gcggccgcga gctcatccag tttatgctt 39

<210> SEQ ID NO 19
<211> LENGTH: 36
<212> TYPE: DNA
<213> ORGANISM: Artificial Sequence
<220> FEATURE:
<223> OTHER INFORMATION: Region IBC (328-405) fragment forward primer used to construct truncated mesothelin mutant

<400> SEQUENCE: 19
agaagaagag aattcgatgc ggccctgctg gccacc 36

<210> SEQ ID NO 20
<211> LENGTH: 39
<212> TYPE: DNA
<213> ORGANISM: Artificial Sequence
<220> FEATURE:
<223> OTHER INFORMATION: Region IBC (328-405) fragment reverse primer used to construct truncated mesothelin mutant

<400> SEQUENCE: 20
ctcttcttct gcggccgcgt gccctttgtt gacttcaag 39

<210> SEQ ID NO 21
<211> LENGTH: 36
<212> TYPE: DNA
<213> ORGANISM: Artificial Sequence
<220> FEATURE:
<223> OTHER INFORMATION: Region IA (296-337) fragment forward primer used to construct truncated mesothelin mutant

<400> SEQUENCE: 21
agaagaagaa agcttgaagt ggagaagaca gcctgt 36

<210> SEQ ID NO 22
<211> LENGTH: 36
<212> TYPE: DNA
<213> ORGANISM: Artificial Sequence
<220> FEATURE:
<223> OTHER INFORMATION: Region IA (296-337) fragment reverse primer used to construct truncated mesothelin mutant

<400> SEQUENCE: 22
tcttcttctg gatccgtcca tctgggtggc cagcag 36

<210> SEQ ID NO 23
<211> LENGTH: 36
<212> TYPE: DNA
<213> ORGANISM: Artificial Sequence
<220> FEATURE:
<223> OTHER INFORMATION: Region IB (328-369) fragment forward primer used to construct truncated mesothelin mutant

<400> SEQUENCE: 23
agaagaagag aattcgatgc ggccctgctg gccacc 36

<210> SEQ ID NO 24
<211> LENGTH: 39
<212> TYPE: DNA
<213> ORGANISM: Artificial Sequence
<220> FEATURE:
<223> OTHER INFORMATION: Region IB (328-369) fragment reverse primer used to construct truncated mesothelin mutant

<400> SEQUENCE: 24
ctcttcttct gcggccgcga tcacagactc ggggtaacc 39

<210> SEQ ID NO 25
<211> LENGTH: 36
<212> TYPE: DNA
<213> ORGANISM: Artificial Sequence
<220> FEATURE:
<223> OTHER INFORMATION: Region IC (360-405) fragment forward primer used to construct truncated mesothelin mutant

<400> SEQUENCE: 25
agaagaagag aattctaccc acaaggttac cccgag 36

<210> SEQ ID NO 26
<211> LENGTH: 39
<212> TYPE: DNA
<213> ORGANISM: Artificial Sequence
<220> FEATURE:
<223> OTHER INFORMATION: Region IC (360-405) fragment reverse primer used to construct truncated mesothelin mutant

<400> SEQUENCE: 26
ctcttcttct gcggccgcgt gccctttgtt gacttcaag 39

<210> SEQ ID NO 27

<211> LENGTH: 93
<212> TYPE: DNA
<213> ORGANISM: Artificial Sequence
<220> FEATURE:
<223> OTHER INFORMATION: Y318A forward PCR mutagenesis primer used to generate alanine replacement mesothelin mutant

<400> SEQUENCE: 27
agaagagaat tcgaagtgga gaagacagcc tgtccttcag gcaagaaggc ccgcgagata 60
gacgagagcc tcatcttcgc caagaagtgg gag 93

<210> SEQ ID NO 28
<211> LENGTH: 39
<212> TYPE: DNA
<213> ORGANISM: Artificial Sequence
<220> FEATURE:
<223> OTHER INFORMATION: Y318A reverse PCR mutagenesis primer used to generate alanine replacement mesothelin mutant

<400> SEQUENCE: 28
ctcttcttct gcggccgcga gctcatccag tttatgctt 39

<210> SEQ ID NO 29
<211> LENGTH: 39
<212> TYPE: DNA
<213> ORGANISM: Artificial Sequence
<220> FEATURE:
<223> OTHER INFORMATION: W321A forward PCR mutagenesis primer used to generate alanine replacement mesothelin mutant

<400> SEQUENCE: 29
tcatcttcta caagaaggcg gagctggaag cctgcgtgg 39

<210> SEQ ID NO 30
<211> LENGTH: 39
<212> TYPE: DNA
<213> ORGANISM: Artificial Sequence
<220> FEATURE:
<223> OTHER INFORMATION: W321A reverse PCR mutagenesis primer used to generate alanine replacement mesothelin mutant

<400> SEQUENCE: 30
ccacgcaggc ttccagctcc gccttcttgt agaagatga 39

<210> SEQ ID NO 31
<211> LENGTH: 108
<212> TYPE: DNA
<213> ORGANISM: Artificial Sequence
<220> FEATURE:
<223> OTHER INFORMATION: E324A forward PCR mutagenesis primer used to generate alanine replacement mesothelin mutant

<400> SEQUENCE: 31
agaagagaat tcgaagtgga gaagacagcc tgtccttcag gcaagaaggc ccgcgagata 60
gacgagagcc tcatcttcta caagaagtgg gagctggcag cctgcgtg 108

<210> SEQ ID NO 32
<211> LENGTH: 39
<212> TYPE: DNA
<213> ORGANISM: Artificial Sequence
<220> FEATURE:
<223> OTHER INFORMATION: E324A reverse PCR mutagenesis primer used to generate alanine replacement mesothelin mutant

<400> SEQUENCE: 32
ctcttcttct gcggccgcga gctcatccag tttatgctt 39

<210> SEQ ID NO 33
<211> LENGTH: 36
<212> TYPE: DNA
<213> ORGANISM: Artificial Sequence
<220> FEATURE:
<223> OTHER INFORMATION: F344A forward PCR mutagenesis primer used to generate alanine replacement mesothelin mutant

<400> SEQUENCE: 33
agaagaagag aattcgaagt ggagaagaca gcctgt 36

<210> SEQ ID NO 34
<211> LENGTH: 75
<212> TYPE: DNA
<213> ORGANISM: Artificial Sequence
<220> FEATURE:
<223> OTHER INFORMATION: F344A reverse PCR mutagenesis primer used to generate alanine replacement mesothelin mutant

<400> SEQUENCE: 34
ttcttctgcg gccgcgagct catccagttt atgctttagg acgtccagct gctcgtaggt 60
ggcggggatg gcgtt 75

<210> SEQ ID NO 35
<211> LENGTH: 36
<212> TYPE: DNA
<213> ORGANISM: Artificial Sequence
<220> FEATURE:
<223> OTHER INFORMATION: E347A forward PCR mutagenesis primer used to generate alanine replacement mesothelin mutant

<400> SEQUENCE: 35
agaagaagag aattcgaagt ggagaagaca gcctgt 36

<210> SEQ ID NO 36
<211> LENGTH: 66
<212> TYPE: DNA
<213> ORGANISM: Artificial Sequence
<220> FEATURE:
<223> OTHER INFORMATION: E347A reverse PCR mutagenesis primer used to generate alanine replacement mesothelin mutant

<400> SEQUENCE: 36
ttcttctgcg gccgcgagct catccagttt atgctttagg acgtccagct gcgcgtaggt 60
gaaggg 66

<210> SEQ ID NO 37
<211> LENGTH: 36
<212> TYPE: DNA
<213> ORGANISM: Artificial Sequence
<220> FEATURE:
<223> OTHER INFORMATION: K353A forward PCR mutagenesis primer used to generate alanine replacement mesothelin mutant

<400> SEQUENCE: 37
agaagaagag aattcgaagt ggagaagaca gcctgt 36

<210> SEQ ID NO 38
<211> LENGTH: 48
<212> TYPE: DNA
<213> ORGANISM: Artificial Sequence
<220> FEATURE:
<223> OTHER INFORMATION: K353A reverse PCR mutagenesis primer used to generate alanine replacement mesothelin mutant

<400> SEQUENCE: 38

-continued

```
ttcttctgcg gccgcgagct catccagttt atgcgctagg acgtccag              48


<210> SEQ ID NO 39
<211> LENGTH: 36
<212> TYPE: DNA
<213> ORGANISM: Artificial Sequence
<220> FEATURE:
<223> OTHER INFORMATION: H354A forward PCR mutagenesis primer used to
      generate alanine replacement mesothelin mutant

<400> SEQUENCE: 39

agaagaagag aattcgaagt ggagaagaca gcctgt                           36


<210> SEQ ID NO 40
<211> LENGTH: 48
<212> TYPE: DNA
<213> ORGANISM: Artificial Sequence
<220> FEATURE:
<223> OTHER INFORMATION: H354A reverse PCR mutagenesis primer used to
      generate alanine replacement mesothelin mutant

<400> SEQUENCE: 40

ctcttcttct gcggccgcga gctcatccag tttagccttt aggacgtc              48


<210> SEQ ID NO 41
<211> LENGTH: 36
<212> TYPE: DNA
<213> ORGANISM: Artificial Sequence
<220> FEATURE:
<223> OTHER INFORMATION: K355A forward PCR mutagenesis primer used to
      generate alanine replacement mesothelin mutant

<400> SEQUENCE: 41

agaagaagag aattcgaagt ggagaagaca gcctgt                           36


<210> SEQ ID NO 42
<211> LENGTH: 48
<212> TYPE: DNA
<213> ORGANISM: Artificial Sequence
<220> FEATURE:
<223> OTHER INFORMATION: K355A reverse PCR mutagenesis primer used to
      generate alanine replacement mesothelin mutant

<400> SEQUENCE: 42

ctcttcttct gcggccgcga gctcatccag tgcatgcttt aggacgtc              48
```

BLOCKING MESOTHELIN PEPTIDE FRAGMENTS

CROSS-REFERENCES TO RELATED APPLICATIONS

The present application is a U.S. National Stage Application of PCT/US2008/085743, filed Dec. 5, 2008, the entire contents of which is incorporated by reference herein in its entirety.

FIELD OF THE INVENTION

The present invention relates to the field of cancer therapy, particularly treating, reversing or preventing cancers mediated by mesothelin-CA125 cell adhesion by the administration of mesothelin peptide fragments that block mesothelin-CA125 interaction, either directly or by eliciting blocking antibodies.

BACKGROUND OF THE INVENTION

Ovarian cancer largely is confined to the peritoneal cavity for much of its natural history (Runowicz, C. D. (2008) *Cancer J.* 14, 7-9). Peritoneal mesothelioma is a highly invasive tumor originating from the mesothelial linings of the peritoneum (Palumbo, et al., (2008) *Curr. Med. Chem.* 15, 855-867). The development of effective drug regimens against ovarian cancer and mesothelioma has proven extremely difficult.

Mesothelin was first identified in 1992 by the monoclonal antibody (mAb) K1 that was generated by the immunization of mice with human ovarian carcinoma (OVCAR-3) cells (Chang, et al., (1992) *Int. J. Cancer* 50, 373-381). It is a glycosyl-phosphatidylinositol (GPI)-anchored glycoprotein present on the cell surface (Chang, K., and Pastan, I. (1996) *Proc. Natl. Acad. Sci. USA* 93, 136-140). The mesothelin gene encodes a 71-kDa precursor protein that is processed to a 40-kDa GPI-anchored protein termed mesothelin. Mesothelin is a differentiation antigen that is present on a restricted set of normal adult tissues such as the mesothelium. In contrast, it is overexpressed in a variety of cancers including mesothelioma, ovarian cancer, and pancreatic cancer (Hassan, R., and Ho, M. (2008) *Eur. J. Cancer* 44, 46-53). It has been demonstrated that mesothelin is also expressed on the surface of non-small cell lung cancer cells (Miettinen, M., and Sarlomo-Rikala, M. (2003) *Am. J. Surg. Pathol.* 27, 150-158; and Ordonez, N. G. (2003) *Am. J. Surg. Pathol.* 27, 1418-1428), especially most lung adenocarcinomas (Ho, et al., (2007) *Clin. Cancer Res.* 13, 1571-1575). We and others have shown that mesothelin is shed from tumor cells (Hellstrom, et al., (2006) *Cancer Epidemiol. Biomarkers Prev.* 15, 1014-1020; and Ho, et al., (2006) *Cancer Epid. Biomarkers Prev.* 15, 1751). Shed serum mesothelin has been approved by the Federal Drug Administration (FDA) as a new diagnostic biomarker in mesothelioma. We have found that antibodies specific for mesothelin are elevated in the sera of patients with mesothelioma and ovarian cancer, and that this elevation is associated with high expression of mesothelin in tumors (Ho, et al., (2005) *Clin. Cancer Res.* 11, 3814-3820). In a phase I clinical study of an intrapleural IFN-β gene transfer using an adenoviral vector in patients with mesotheliomas, antitumor immune responses targeting mesothelin were elicited in several patients (Sterman, et al., (2007) *Clin. Cancer Res.* 13, 4456-4466). A recent study indicated that anti-mesothelin antibodies and circulating mesothelin relate to the clinical state in ovarian cancer patients (Hellstrom, et al., (2008) *Cancer Epidemiol. Biomarkers Prev.* 17, 1520-1526).

Pastan and colleagues developed an immunotoxin (SS1P) with a high affinity Fv for mesothelin (Pastan, et al, (2006) *Nat. Rev. Cancer* 6, 559-565). Two phase I clinical trials were completed at the National Cancer Institute (NIH, Bethesda, Md.) and there was sufficient antitumor activity of SS1P to justify a phase II trial. MORAb-009 is a high-affinity chimeric (mouse/human) monoclonal IgG1/κ containing the same Fv (SS1) for mesothelin. A Phase I clinical trial of MORAb-009 has been initiated in patients with ovarian cancer, mesothelioma, pancreatic cancer, and non-small cell lung cancer (Hassan, et al., (2007) *Cancer Immun.* 7, 20).

There is evidence that in mouse mammary epithelial cells activation of the Wnt signaling pathway can lead to an increase in mesothelin expression (Prieve, M. G., and Moon, R. T. (2003) *BMC Dev. Biol.* 3, 2). This may well explain the fact that mesothelioma and ovarian cancer with constitutive activation of Wnt signaling have high mesothelin expression. The biological functions of mesothelin remain elusive. The mesothelin knockout mice did not have a detectable phenotype (Bera, T. K., and Pastan, I. (2000) *Mol. Cell. Biol.* 20, 2902-2906).

Mucins are heavily glycosylated proteins found in the mucus layer or at the cell surface of many epitheliums (Desseyn, J. L., Tetaert, D., and Gouyer, V. (2008) *Gene* 410, 215-222). There are two structurally distinct families of mucins, secreted and membrane-bound forms. CA125 (also known as MUC16) was first identified in 1981 by OC125, a mAb that had been developed from mice immunized with human ovarian cancer cells (Bast, et al., (1981) *J. Clin. Invest.* 68, 1331-1337). The first cDNA clones were reported in 2001 (Yin, B. W. T., and Lloyd, K. O. (2001) *J. Biol. Chem.* 276, 27371-27375; and O'Brien, et al., (2001) *Tumour Biol.* 22, 348-366). It is a very large membrane-bound cell surface mucin, with an average molecular weight between 2.5 and 5 million Dalton. It is also heavily glycosylated with both O-linked and N-linked oligosaccharides (O'Brien, et al., (2002) *Tumour Biol.* 23, 154-169). It is shed into the serum and is used for monitoring response to therapy in ovarian cancer (Bast, et al., (1983) *N. Engl. J. Med.* 309, 883-887). The peptide backbone of CA125 is composed of the N-terminal region, extensive Ser/Thr/Pro-rich tandem repeats (TR) with 156 amino acids each with both N- and O-glycosylations, a SEA domain with high levels of O-glycosylation and a C-terminal region with a short cytoplasmic tail (O'Brien, et al., (2001) *Tumour Biol.* 22, 348-366). The SEA domain was first identified as a module commonly found in sea urchin sperm protein, enterokinase and agrin (Bork, P., and Patthy, L. (1995) Protein Sci. 4, 1421-1425; and Maeda, et al., (2004) *J. Biol. Chem.* 279, 13174-13182). The significance of the SEA domain in CA125 is not clear.

CA125 was originally used as a biomarker in ovarian cancer due to its high expression in ovarian carcinomas. A majority (88%) of mesotheliomas are also CA125 positive on the cell membrane (Bateman, et al., (1997) *Histopathology* 30, 49-56). It was shown that 25% of peritoneal mesotheliomas have high CA125 expression (Attanoos, et al., (2002) *Histopathology* 40, 237-244). The intensity of CA125 membranous expression is indistinguishable between ovarian carcinomas and peritoneal mesotheliomas. Gene expression analysis using SAGE tag database has shown that mesothelioma has the second highest co-expression of CA125 and mesothelin after ovarian cancer (Rump, et al., (2004) *J. Biol. Chem.* 279, 9190-9198). Rump and colleagues have shown that mesothelin binds to CA125 and that this interaction may mediate cell adhesion (Rump, et al., supra). Since mesothelin is present on peritoneal mesothelium, there may be an important role for the mesothelin-CA125 interaction in tumorigenesis of ovarian cancer or mesothelioma in the peritoneal cavity. Scholler et al. recently showed that CA125/mesothelin-dependent cell attachment could be blocked with anti-CA125 antibodies (Scholler, et al., (2007) *Cancer Lett.* 247, 130-136). The mesothelin binding site on CA125 may lie within the 156 amino acid TR units, indicating multimeric binding of mesothelin to CA125. It has been found that the extraordinarily abundant N-glycans on CA125, presumably in the TR region, are required for binding to both glycosylated and non-glycosylated mesothelin (Gubbels, et al, (2006) *Mol. Cancer.* 5, 50).

There remains a need for pharmacological agents that effectively disrupt binding between CA125 and mesothelin and cell adhesion mediated by the CA125/mesothelin interaction.

BRIEF SUMMARY OF THE INVENTION

The present invention provides mesothelin peptide fragments that disrupt the binding interaction between mesothelin and CA125, either directly by binding to CA125 or indirectly by inducing antibodies in a subject that specifically bind to mesothelin (i.e., in particular the CA125 binding region of mesothelin). Accordingly, in one aspect, the present invention provides polypeptides comprising a mesothelin fragment no longer than (i.e., in terms of the number of residues) amino acid residues 296-390 (i.e., region I) of mesothelin (e.g., residues 296-390 of SEQ ID NO:1), wherein the polypeptide specifically binds to CA125. In some embodiments, the mesothelin fragment is no longer than amino acid residues 1-95 of SEQ ID NO: 9 (the mesothelin consensus sequence depicted in FIG. 2). In some embodiments, the mesothelin peptide fragment has flanking amino acids or polypeptide sequences that are other than mesothelin.

In some embodiments, the mesothelin fragment is no longer than amino acid residues 296-359 of mesothelin (e.g., residues 296-359 of SEQ ID NO:1). In some embodiments, the mesothelin fragment is no longer than amino acid residues 1-64 of SEQ ID NO: 9 (the mesothelin consensus sequence depicted in FIG. 2). In some embodiments, the mesothelin fragment comprises the amino acid sequence EVEKTACPSGKKAREIDESLIFYKKXELXACVDAALLATQMDRVNAIPFTYEQLDVLKXKLDEL (SEQ ID NO:2), wherein X is any amino acid. In some embodiments, the mesothelin fragment comprise the amino acid sequence EVEKTACPSGKKAREIDESLIFYKKWELEACVDAALLATQMDRVNAIPFTYEQLDVLKHKLDEL (SEQ ID NO:3).

In some embodiments, the polypeptide is a fusion polypeptide comprising the mesothelin fragment and a second polypeptide, wherein the second polypeptide is not mesothelin. In some embodiments, the second polypeptide is selected from the group consisting of an Fc portion of an antibody, a cytokine, a chemokine, a carrier protein, a cytotoxin and an enzyme. In some embodiments, the second polypeptide is an Fc portion of an antibody.

In a further aspect, the invention provides compositions comprising a mesothelin fragment no longer than amino acid residues 296-390 (i.e., region I) of mesothelin, wherein the polypeptide specifically binds to CA125, and a pharmaceutically acceptable excipient. Further embodiments of the polypeptide and mesothelin fragment are as described above and herein. In some embodiments, the compositions further comprise an adjuvant.

In a related aspect, the invention provides methods of inhibiting CA125/mesothelin-dependent cell attachment comprising contacting a cell expressing CA125 with a polypeptide comprising a mesothelin fragment no longer than amino acid residues 296-390 of mesothelin. Further embodiments of the polypeptide and mesothelin fragment are as described above and herein.

In another aspect, the invention provides methods of inhibiting a cancer mediated by CA125/mesothelin-dependent cell attachment comprising contacting a cell expressing CA125 with a polypeptide comprising a mesothelin fragment no longer than amino acid residues 296-390 of mesothelin. Further embodiments of the polypeptide and mesothelin fragment are as described above and herein. In some embodiments, the cancer is selected from the group consisting of ovarian cancer, mesothelioma, non-small cell lung cancer, lung adenocarcinoma and pancreatic cancer.

In some embodiments, the inhibiting step is performed in vitro. In some embodiments, the inhibiting step is performed in vivo.

In some embodiments, the mesothelin fragment is administered under a regime such that the mesothelin fragment directly binds to CA125, thereby inhibiting CA125/mesothelin-dependent cell attachment. In some embodiments, the mesothelin fragment is administered intraperitoneally or intratumorally.

In some embodiments, the mesothelin fragment is administered under a regime such that the mesothelin fragment elicits antibodies that specifically bind to mesothelin, thereby inhibiting CA125/mesothelin-dependent cell attachment. In some embodiments, the mesothelin fragment is administered intradermally or subcutaneously. In some embodiments, an adjuvant is co-administered.

DEFINITIONS

The terms "subject," "patient," "individual" refer to a mammal, for example a human or a non-human primate (e.g., chimpanzee, macaque, orangutan). The mammal can also be a domesticated mammal (e.g., feline, canine), an agricultural mammal (e.g., bovine, equine, porcine, ovine) or a laboratory mammal (e.g., lagomorpha, rattus, murine, hamster).

A cancer "mediated by CA125/mesothelin binding" or requiring "CA125/mesothelin mediated cell adhesion" refers to cancers whose growth, spread or progression can be partially or wholly inhibited or reduced by interfering with or blocking the binding interaction of CA125 to mesothelin. Such cancers may have tumor cells that overexpress or express high levels of mesothelin and/or CA125, e.g., in comparison to normal cells of the same tissue type or in comparison to cancer cells of distinct tissue types. Exemplary cancers whose growth, spread and/or progression are at least partially mediated by CA125/mesothelin binding include ovarian cancer, mesothelioma, non-small cell lung cancer, lung adenocarcinoma and pancreatic cancer.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to administration of a mesothelin peptide fragment. In some embodiments, the growth, progression or spread of a tumor or cancer is inhibited, reduced or decreased by at least about 1-fold, 2-fold, 3-fold, 4-fold, or more in comparison to the tumor burden prior to administration of a mesothelin peptide fragment.

The term "co-administered" refers to two active pharmacological agents in the blood or body tissues of a host at the same time. Co-administered agents can be concurrently administered, or sequentially administered.

For purposes of classifying amino acids substitutions as conservative or nonconservative, amino acids are grouped as follows: Group I (hydrophobic sidechains): norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

A "fusion polypeptide" refers to a polypeptide comprised of two or more heterologous polypeptides, e.g., a mesothelin peptide fragment and one or more additional polypeptides other than mesothelin. The two or more polypeptides comprising the fusion polypeptide can directly abut one another or be joined through a linker or spacer sequence. In a fusion polypeptide comprising a mesothelin peptide fragment, the mesothelin peptide fragment can be situated at the N-terminus, in the center between two other polypeptides, or at the C-terminus.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity. In some embodiments, the agent is a mesothelin peptide fragment corresponding to the CA125 binding region of mesothelin, as described herein.

Therapeutic agents of the invention are typically substantially pure from undesired contaminant. This means that an agent is typically at least about 50% w/w (weight/weight) purity, as well as being substantially free from interfering proteins and contaminants Sometimes the agents are at least about 80% w/w and, more preferably at least 90 or about 95% w/w purity. However, using conventional protein purification techniques, homogeneous peptides of at least 99% w/w can be obtained. Therapeutic agents of the invention can prevent, effect prophylaxis of, inhibit, reduce or treat a cancer mediated by mesothelin-CA125 cell adhesion.

Specific binding between two entities means the entities have a mutual affinity for each other that is at least 10-, 100- or 1000-fold greater than the affinity of either entity for a control, such as unrelated antigen or antibody to a different antigen. The mutual affinity of the two entities for each other is usually at least $10^7$, $10^8$, $10^9$ $M^{-1}$, or $10^{10} M^{-1}$. Affinities greater than $10^8$ $M^{-1}$ are preferred. Specific binding of a polyclonal antibody to an epitope within mesothelin or within the CA125 binding site of mesothelin means the antibodies in the polyclonal antibody population specifically bind to one epitope of mesothelin or within the CA125 binding site of mesothelin without binding to other epitopes of mesothelin.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' $F(ab')_2$, Fabc, and FAT. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol 148, 1547-1553 (1992).

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis., 170, 1110-19 (1994)), by antigen-dependent killing (cytotoxic T lymphocyte assay, Tigges et al., J. Immunol., 156, 3901-3910) or by cytokine secretion.

The term "immunological" or "immune" response is the development of a beneficial humoral (antibody mediated) and/or a cellular (mediated by antigen-specific T cells or their secretion products) response directed against a mesothelin peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4+ T cells) or CTL (cytotoxic T lymphocyte) assays (see Burke, supra; Tigges, supra). The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

Competition between antibodies is determined by an assay in which the immunoglobulin under test inhibits specific binding of a reference antibody to a common antigen, such as mesothelin. Competitive assays can also be performed with mesothelin peptide fragments, wherein a mesothelin peptide fragment competes, e.g., with a full-length mesothelin polypeptide or another methothelin peptide fragment for binding to CA125 (or fragment thereof).

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology, 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using 1-125 label (see Morel et al., Molec. Immunol. 25(1):7-15 (1988)); solid phase direct biotin-avidin EIA (Cheung et al., Virology, 176:546-552 (1990)); and direct labeled RIA (Moldenhauer et al., Scand. J. Immunol., 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

An antibody that specifically binds to mesothelin means an antibody that binds to mesothelin with an affinity of at least $10^7$ $M^{-1}$. Some antibodies bind to mesothelin with affinities between $10^8$ $M^{-1}$ and $10^{11}$ $M^{-1}$.

Compositions or methods "comprising" one or more recited elements may include other elements not specifically recited. For example, a composition that comprises a mesothelin peptide encompasses both an isolated mesothelin peptide and a mesothelin peptide as a component of a larger polypeptide sequence.

Compositions or methods "consisting essentially of" one or more recited elements include the elements specifically recited and may further include pharmacologically inactive components (e.g., excipients, vehicles), but do not include unrecited pharmacologically active agents.

DETAILED DESCRIPTION

1. Introduction

Figure 1:
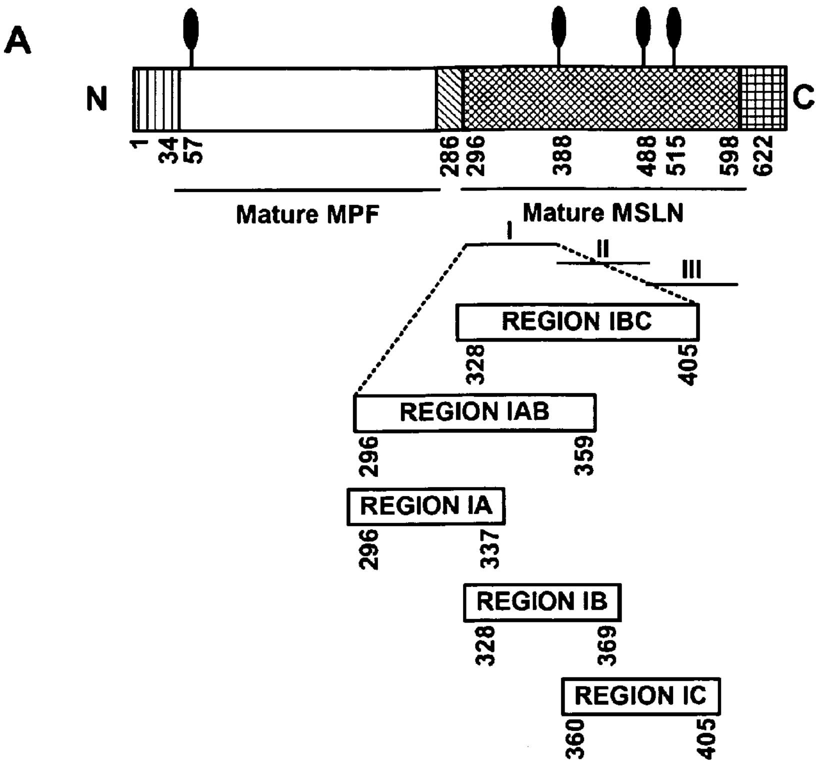
FIGS. 1A-B. Generation of truncated and alanine replacement mutants of mesothelin. A. The mesothelin (MSLN) gene encodes a precursor protein of 622 amino acids. On translocation into the endoplasmic reticulum the N-terminal signal peptide (vertical lines; residues 1-33) and the C-terminal GPI anchor addition signal (blue; a predicted cleavage site: Ser598) are removed and the latter replaced with a GPI anchor. The MSLN precursor (71-kDa) is cleaved into two products, the 30-kDa megakaryocyte potentiating factor (MPF; residues Ser34-Arg286) (Kojima, et al., (1995) *J. Biol. Chem.* 270, 21984-21990) and the 41-kDa GPI-anchored membrane-bound mature MSLN (cross-hatching) starting from Glu296. The proteolytic cleavage region (diagonal lines) contains a furin cleavage site at Arg295, and other protease cleavage sites including a trypsin cleavage site at Arg286. The four predicted N-linked glycans (black lollipops; Asn57, Asn388, Asn488 and Asn515) on mesothelin are indicated. Truncated mutants (Regions I, II, III, IAB, IBC, IA, IB and IC) were generated as rFc fusion proteins to sequentially narrow down the CA125 binding domain of mesothelin. B. Mesothelin and truncated mutants were generated using a modified pSecTag2B vector that when transfected into HEK 293T cells created secreted rFc-fusion proteins. A CMV promoter (PCMV) drove the expression of an Ig-κ signal, followed by a rFc fragment, a thrombin cleavage site and the desired portion of mesothelin. A 6×His tag (SEQ ID NO:6) was added at the C-terminal of the construct.
Figure 1:
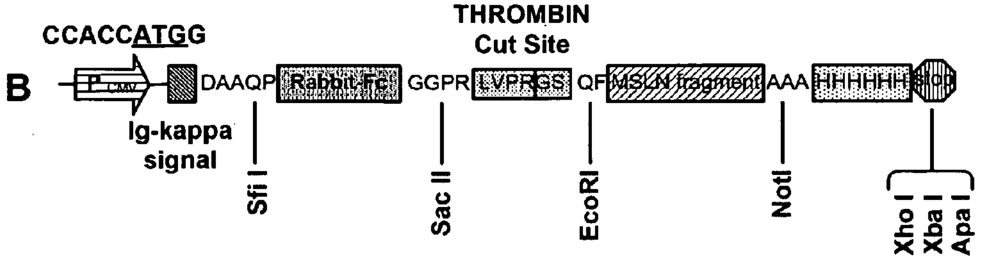

The present invention provides peptide fragments of mesothelin that contain the binding site of CA125 on mesothelin. The mesothelin peptide fragments find use in inhibiting the binding interaction between CA125 and mesothelin, both directly (e.g., by competitively binding to CA125) and indirectly (e.g., by inducing antibodies that specifically bind to the CA125 binding region of mesothelin and disrupt interaction between CA125 and mesothelin).

Ovarian cancer and malignant mesothelioma frequently express both mesothelin and CA125 (also known as MUC16) at high levels on the cell surface. The interaction between mesothelin and CA125 facilitates the implantation and peritoneal spread of tumors by cell adhesion, whereas the detailed nature of this interaction is still unknown. Here, we used truncated mutagenesis and alanine replacement techniques to identify a binding site on mesothelin for CA125. We examined the molecular interaction by Western blot overlay assays and further quantitatively analyzed by enzyme-linked immunosorbent assay. We also evaluated the binding on cancer cells by flow cytometry. We identified the region (296-359) consisting of 64 amino acids at the N terminal of cell surface mesothelin as the minimum fragment for complete binding activity to CA125. In addition, we found that substitution of tyrosine-318 with an alanine abolished the CA125-binding. Replacement of tryptophan-321 and glutamic acid-324 with alanine could partially decrease binding to CA125, while mutation of histidine-354 had no effect. These results indicate that a conformation-sensitive structure of the region (296-359) is required and sufficient for the binding of mesothelin to CA125. The CA125-binding domain is likely to have helical secondary structures.

2. Compositions a. Polypeptides Comprising Therapeutically Useful Mesothelin Fragments i. Mesothelin Fragments The mesothelin fragments of the invention find use in blocking binding of mesothelin to CA125 (MUC16). The mesothelin peptide fragments described herein can directly block mesothelin binding to CA125, e.g., by binding to CA125 and competing with the binding of, e.g., full-length or cell-anchored mesothelin. The mesothelin peptide fragments can also be used as vaccines in active immunization regimes that elicit antibodies that specifically bind to an epitope of mesothelin that is required for binding to CA125.

The mesothelin fragments of the invention correspond to the CA125 binding site on mesothelin, and therefore find use in competitively blocking the binding of mesothelin to CA125. For the purposes of blocking and active immunization, the mesothelin peptide fragments are no longer than mesothelin amino acid residues 296-390 (i.e., Region I), and can be shorter peptide fragments. The numbering of the mesothelin residues is in accordance with what is understood in the art and with reference to SEQ ID NO:1, or GenBank Accession No. CAC37289. For example, in some embodiments, the N-terminus of the peptide fragment begins at mesothelin amino acid residue 296 and the C-terminus ends at a mesothelin amino acid residue within the range of from 359 to 390. In some embodiments, the mesothelin fragment is no longer than mesothelin amino acid residues 296-359 (i.e., Region IAB). In some embodiments, the mesothelin peptide fragment has an N-terminus that begins at a mesothelin amino acid residue within the range of 286-306 and has a C-terminus that ends at a mesothelin amino acid residue within the range of 349-369.

For the purposes of active immunization, subfragments of 7-9 contiguous amino acids within mesothelin amino acid residues 296-359 (i.e., Region IAB) can be used to generate a high immunogenic response to the mesothelin binding site for CA125.

In some embodiments, up to 1%, 2%, 3%, 4% or 5% or up to 1, 2, 3, 4, 5 or 6 amino acids are substituted, added or deleted within a peptide fragment. This corresponds to at least 90%, 95%, 96%, 97%, 98% or 99% sequence identity as measured using an alignment algorithm known in the art (e.g., BLAST, ALIGN) set to default settings. Preferred substitutions are conservative and do not affect or minimally affect the intended function of the peptide fragment to directly block CA125 binding to mesothelin or to induce antibodies against the CA125 binding domain of mesothelin. Amino acid residues that can be altered while not diminishing the function of the peptide fragment to bind to CA125 can be determined using methods well known in the art, including those described here (e.g., alanine substitution). For example, amino acid residues Trp321, Glu324 and His354 can be deleted or substituted conservatively or non-conservatively without affecting the CA125 binding function of the peptide fragment. In some embodiments, amino acid residues Tyr318 and Glu324 are not altered or deleted. In some embodiments, amino acid residues Phe344, Glu347, Lys353 and Lys355 are not altered or deleted.

Unless otherwise indicated, reference to mesothelin peptide fragments includes the natural human amino acid sequences indicated above as well as analogs including allelic, species and induced variants. Analogs of mesothelin induce antibodies that specifically bind with a natural mesothelin peptide. Analogs of mesothelin typically differ from naturally occurring peptides at up to 30%, e.g., up to 20% or 10%, of amino acid positions or by up to 1, 2, 3, 4, 5, 6, 7, 8, 9 or 10 position changes. For example, in some embodiments, an analog of mesothelin 296-359 may vary by up to 1, 2, 3, 4, 5 or 6 position changes. Each deletion or substitution of a natural amino acid residue is considered a position change as is the insertion of a residue without substitution. Amino acids substitutions are often conservative.

Some analogs of mesothelin fragments also include unnatural amino acids or modifications of N or C terminal amino acids at one, two, five, ten or even all positions. For example, a natural aspartic acid residue can be replaced with iso-aspartic acid. Examples of unnatural amino acids include D, alpha, alpha-disubstituted amino acids, N-alkyl amino acids, lactic acid, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, β-alanine, ornithine, norleucine, norvaline, hydroxproline, thyroxine, gamma-amino butyric acid, homoserine, citrulline, and isoaspartic acid. Some therapeutic agents of the invention are all-D mesothelin fragments, and/or all-D mesothelin peptide analogs. Fragments and analogs can be screened for prophylactic or therapeutic efficacy in animal models of cancers mediated by mesothelin/CA125 cell adhesion, in comparison with untreated or placebo controls as described below.

Mesothelin fragments and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., Molecular Cloning: A Laboratory Manual (C.S.H.P. Press, NY 3rd ed., 2001).

Therapeutic agents also include longer polypeptides that include, for example, an immunogenic and/or blocking fragment of mesothelin peptide, together with one or more other amino acids flanking the mesothelin peptide on one or one or both sides. Exemplary agents include fusion proteins comprising a segment of mesothelin fused to a heterologous amino acid sequence that induces a helper T-cell response against the heterologous amino acid sequence and thereby a B-cell response against the mesothelin segment. One or more flanking heterologous amino acids can also be used to cap an mesothelin peptide fragment to protect it from degradation in manufacture, storage or use. Such polypeptides can be screened for prophylactic or therapeutic efficacy in animal models in comparison with untreated or placebo controls as described below. Therapeutic agents of the invention include an immunogenic fragment of mesothelin flanked by polylysine sequences. The polylysine sequences can be fused to the N-terminus, the C terminus, or both the N- and C-terminus of an immunogenic and/or blocking fragment of mesothelin. The mesothelin peptide, analog, active fragment or other polypeptide can be administered in associated or multimeric form or in dissociated form. Therapeutic agents also include multimers of monomeric immunogenic agents.

In a further variation, an immunogenic fragment of mesothelin can be presented by a virus or a bacteria as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include *Salmonella* and *Shigella*. Fusion of an immunogenic peptide to HBsAg of HBV is particularly suitable.

Therapeutic agents also include peptides and other compounds that do not necessarily have a significant amino acid sequence similarity with mesothelin but nevertheless serve as mimetics of mesothelin and induce a similar immune response. For example, any peptides and proteins forming β-pleated sheets can be screened for suitability. Anti-idiotypic antibodies against monoclonal antibodies to mesothelin peptides can also be used. Such anti-Id antibodies mimic the antigen and generate an immune response to it (see Essential Immunology (Roit ed., Blackwell Scientific Publications, Palo Alto, 6th ed.), p. 181). Agents other than mesothelin peptides can be used to block mesothelin-CA125 binding or induce an immunogenic response against the CA125 binding region of mesothelin (e.g., one or more epitopes within mesothelin 296-359). Preferably, such agents induce an immunogenic response that is specifically directed to one of these segments without being directed to other segments of mesothelin.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to specifically bind to antibodies or lymphocytes (B or T) known to be specific for the CA125 binding region of mesothelin. For example, initial screens can be performed with any polyclonal sera or monoclonal antibody to the CA125 binding region of mesothelin. Compounds can then be screened for specifically binding to a specific epitope within mesothelin residues 296-359 or for the ability to inhibit binding between mesothelin and CA125. Compounds can be tested by the same procedures described for mapping antibody epitope specificities. Compounds identified by such screens are then further analyzed for capacity to induce antibodies or reactive lymphocytes to mesothelin or fragments thereof. For example, multiple dilutions of sera can be tested on microtiter plates that have been precoated with mesothelin or a fragment thereof and a standard ELISA can be performed to test for reactive antibodies to mesothelin or the fragment. Compounds can then be tested for prophylactic and therapeutic efficacy in animals suffering from or predisposed to (e.g., in remission from) a cancer mediated by mesothelin/CA125 interaction, as described in the Examples. Such animals models are known in the art and include without limitation, human tumor xenograft or metastatic tumor models using human ovarian cancer cells (e.g., OVCAR3 cells (Flessner, et al., *Clin Cancer Res*. (2005) 11(8):3117-25; Belotti, et al., *Cancer Res*. (2003) 63(17):5224-9; Manetta, et al., *Gynecol Oncol*. (1989) 32(3):368-70) or human malignant mesothelioma tumors (Inamoto, et al., *Clin Cancer Res*. (2007) 13(14):4191-200; Schulten, et al., *Cancer Genet Cytogenet*. (2007) 176(1):35-47; Spugnini, et al., *Clin Cancer Res*. (2006) 12(20 Pt 1):6133-43).

ii. Conjugates Comprising Mesothelin Fragments

The mesothelin peptide fragments of the invention may be linked to a second polypeptide other than mesothelin or to another active agent (e.g., a drug, a radionuclide) desirable to deliver to cells that overexpress mesothelin. The mesothelin fragment and the second polypeptide can be chemically linked or produced as a fusion protein. Chemical linkers for joining two polypeptides are known in the art, as described in more detail below. In some embodiments, the mesothelin peptide fragment is linked to a anticancer chemotherapeutic drug, for example, vincristine, vinblastine, doxorubicin, or 5-fluorouracil.

The second polypeptide can be, for example, an Fc portion of an antibody (e.g., to induce antibody-dependent cell cytotoxicity (ADCC)), a cytotoxin, a cytokine, a chemokine, and an enzyme.

Exemplary cytokines include Th1 cytokines and pro-inflammatory cytokines, for example, IL-1α and β peptides, IL-2, IL-6, IL-12, IL-13, and IL-15, interferons including interferon-alpha (IFN-α), interferon-beta (IFN-β), interferon-gamma (IFN-γ); macrophage colony stimulating factor (M-CSF), granulocyte-macrophage colony stimulating factor (GM-CSF), and tumor necrosis factor (TNF). Chemokine polypeptides suitable in mesothelin peptide fragment conjugates include, without limitation, interferon-induced protein 10 (IP-10), monocyte chemotactic protein-1 (MCP-1), MCP-2, MCP-3, MCP-4, macrophage inflammatory protein 1 (MIP1), MIP2, MIP3, RANTES (CC chemokine ligand 5), macrophage-derived chemokine (MDC), stromal cell-derived factor 1 (SDF-1), monokine induced by IFN-gamma (MIG), as well as any other chemokine now known or later identified.

Exemplary cytotoxins include *Pseudomonas* exotoxins, Diphtheria toxins, ricin, and abrin. *Pseudomonas* exotoxin and Diphtheria toxin are most preferred. Suitable *Pseudomonas* exotoxin variants for use in delivery to tumor cells are well known in the art and described, for example, in U.S. Pat. Nos. 4,545,985; 5,458,878; 5,602,095; 5,705,163; 5,980,895; 6,074,644; 6,423,513; 6,426,075 and 6,518,061.

iii. Carrier Polypeptides Comprising Mesothelin Fragments

Some agents for inducing an immune response contain the appropriate epitope for inducing an immune response against mesothelin but are too small to be immunogenic. In this situation, a mesothelin peptide immunogen can be linked to a suitable carrier molecule to form a conjugate which helps elicit an immune response. A single agent can be linked to a single carrier, multiple copies of an agent can be linked to multiple copies of a carrier, which are in turn linked to each other, multiple copies of an agent can be linked to a single copy of a carrier, or a single copy of an agent can be linked to multiple copies of a carrier, or different carriers. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine ($Pam_3Cys$), mannan (a manse polymer), or glucan (a beta 1→2 polymer)), cytokines (e.g., IL-1, IL-1alpha and beta peptides, IL-2, gamma-INF, IL-10, GM-CSF), and chemokines (e.g., MIP1alpha and beta, and RANTES) Immunogenic agents can also be linked to peptides that enhance transport across tissues, as described in O'Mahony, WO 97/17613 and WO 97/17614. Immunogens may be linked to the carriers with or without spacers amino acids (e.g., Gly-Gly).

Some conjugates can be formed by linking agents of the invention to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, *Chlamydia trachomitis* major outer membrane protein, diphtheria toxoid, *Plasmodium falciparum* circumsporozite T, *Plasmodium falciparum* CS antigen, *Schistosoma mansoni* triose phosphate isomersae, *Eschericlia coli* TraT, and Influenza virus hemagluttinin (HA). The immunogenic peptides of the invention can also be conjugated to the T-cell epitopes described in Sinigaglia F. et al., Nature, 336: 778-780 (1988); Chicz R. M. et al., J. Exp. Med., 178:27-47 (1993); Hammer J. et al., Cell 74:197-203 (1993); Falk K. et al., Immunogenetics, 39:230-242 (1994); WO 98/23635; and, Southwood S. et al. J. Immunology, 160:3363-3373 (1998) (each of which is incorporated herein by reference for all purposes). Further examples are disclosed in, e.g., WO 2004/069182.

Alternatively, the conjugates can be formed by linking agents of the invention to at least one artificial T-cell epitope capable of binding a large proportion of MHC Class II molecules, such as the pan DR epitope ("PADRE"). PADRE is described in U.S. Pat. No. 5,736,141, WO 95/07707, and Alexander J et al., Immunity, 1:751-761 (1994) (each of which is incorporated herein by reference for all purposes). A preferred PADRE peptide is AKXVAAWTLKAAA (SEQ ID NO:10), wherein X is preferably cyclohexylalanine, tyrosine or phenylalanine, with cyclohexylalanine being most preferred.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-maleimido-methyl)cyclohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the $T_h$ epitope and the peptide immunogen of the invention. In addition to physically separating the $T_h$ epitope from the B cell epitope (i.e., the peptide immunogen), the glycine residues can disrupt any artificial secondary structures created by the joining of the $T_h$ epitope with the peptide immunogen, and thereby eliminate interference between the T and/or B cell responses. The conformational separation between the helper epitope and the antibody eliciting domain thus permits more efficient interactions between the presented immunogen and the appropriate $T_h$ and B cells.

To enhance the induction of T cell immunity in a large percentage of subjects displaying various HLA types to an agent of the present invention, a mixture of conjugates with different $T_h$ cell epitopes can be prepared. The mixture may contain a mixture of at least two conjugates with different $T_h$ cell epitopes, a mixture of at least three conjugates with different $T_h$ cell epitopes, or a mixture of at least four conjugates with different $T_h$ cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Optionally, multiple copies of an immunogenic peptide can be linked to multiple copies of a heterologous peptide which are linked to each other. Some carrier peptides serve to induce a helper T-cell response against the carrier peptide. The induced helper T-cells in turn induce a B-cell response against the immunogenic peptide linked to the carrier.

The same or similar carrier proteins and methods of linkage can be used for generating immunogens to be used in generation of antibodies against mesothelin fragments. For example, an immunogenic fragment of mesothelin linked to a carrier can be administered to a laboratory animal in the production of monoclonal antibodies to mesothelin or an immunogenic fragment of mesothelin.

iv. Nucleic Acids Encoding Mesothelin Fragments

Immune responses against the CA125 binding region of mesothelin can also be induced by administration of nucleic acids encoding fragments of mesothelin as described herein. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors. The nucleic acids encoding therapeutic agents of the invention can also encode at least one T cell epitope. The disclosures herein which relate to the use of adjuvants and the use of carriers apply mutatis mutandis to their use with the nucleic acids encoding the therapeutic agents of the present invention.

A number of viral vector systems are available including retroviral systems (see, e.g., Lawrie and Tumin, Cur. Opin. Genet. Develop. 3, 102-109 (1993)); adenoviral vectors (see, e.g., Bett et al., J. Virol. 67, 5911 (1993)); adeno-associated virus vectors (see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubenslcy et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al., WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. Nos. 5,208,036; 5,264,618; 5,279,833 and 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee, et al., J. Micro Encap. (1996).

Gene therapy vectors or naked DNA can be delivered in vivo by administration to an individual patient, typically by systemic administration (e.g. intravenous, intraperitoneal, nasal, gastric, intradermal, intramuscular, subdermal, or intracranial infusion) or topical application (see e.g., U.S. Pat. No. 5,399,346). Such vectors can further include facilitating agents such as bupivacine (U.S. Pat. No. 5,593,970). DNA can also be administered using a gene gun. (See Xiao & Brandsma, supra.) The DNA encoding an immunogen is precipitated onto the surface of microscopic metal beads. The microprojectiles are accelerated with a shock wave or expanding helium gas, and penetrate tissues to a depth of several cell layers. For example, The Accel™. Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

b. Pharmaceutical Compositions i. Formulations

Agents of the invention are often administered as pharmaceutical compositions comprising an active therapeutic agent, i.e., and a variety of other pharmaceutically acceptable components. See, Remington: The Science and Practice of Pharmacy, $21^{st}$ Ed., 2005, University of the Sciences in Philadelphia (USIP). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or non-toxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. An exemplary buffered liquid composition comprises a mesothelin peptide fragment at 5 mg/mL, formulated in aqueous buffer consisting of 50 mM L-histidine, 150 mM NaCl, adjusted to pH 6.0 with HCl. Composition for parenteral administration are typically substantially sterile, isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997)). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., Eur. J. Immunol. 25, 3521-24 (1995); Cevc et al., Biochem. Biophys. Acta 1368, 201-15 (1998)).

ii. Adjuvants

Immunogenic agents of the invention, such as peptides, are sometimes administered in combination with an adjuvant. The adjuvant increases the titer of induced antibodies and/or the binding affinity of induced antibodies relative to the situation if the peptide were used alone. A variety of adjuvants can be used in combination with an immunogenic fragment of mesothelin, to elicit an immune response. Exemplary adjuvants augment the intrinsic response to an immunogen without causing conformational changes in the immunogen that affect the qualitative form of the response. Exemplary adjuvants include aluminum hydroxide and aluminum phosphate, 3 De-O-acylated monophosphoryl lipid A (MPL™) (see GB 2220211). Stimulon™ QS-21 is a triterpene glycoside or saponin isolated from the bark of the Quillaja Saponaria Molina tree found in South America (see Kensil et al., in Vaccine Design: The Subunit and Adjuvant Approach (eds. Powell & Newman, Plenum Press, NY, 1995); U.S. Pat. No. 5,057,540), (Aquila BioPharmaceuticals, Framingham, Mass.). Other adjuvants include oil in water emulsions (such as squalene or peanut oil), optionally in combination with immune stimulants, such as monophosphoryl lipid A (see Stoute et al., N. Engl. J. Med. 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g. N-acetylmuramyl-L-threonyl-D-isoglutamine (thr-MDP), N-acetyl-normuramyl-L-alanyl-D-isoglutamine (nor-MDP), muramylNAc-alanyl-isoglutaminyl-lysine-tripeptide-PE (MTP-PE), N-acetylglucosaminyl-N-acetylmuramyl-L-alanyl-D-isoglutaminyl-L-alanyl-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryl lipid A (MPL), trehalose dimycolate (IDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX®. Other adjuvants include RC-529, GM-CSF and Complete Freund's Adjuvant (CFA) and Incomplete Freund's Adjuvant (IFA). Other adjuvants include cytokines, such as interleukins (e.g., IL-1α and β peptides, IL-2, IL-4, IL-6, IL-12, IL-13, and IL-15), macrophage colony stimulating factor (M-CSF), granulocyte-macrophage colony stimulating factor (GM-CSF), tumor necrosis factor (TNF), chemokines, such as MIP1α and β and RANTES. Another class of adjuvants is glycolipid analogues including N-glycosylamides, N-glycosylureas and N-glycosylcarbamates, each of which is substituted in the sugar residue by an amino acid, as immunomodulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred for human administration. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., Advanced Drug Delivery Reviews 32, 173-186 (1998)), optionally in combination with any of alum, QS-21, and MPL and all combinations thereof.

3. Methods of Inhibiting CA125-Mesothelin Interaction a. Conditions Subject to Treatment

The mesothelin peptide fragments corresponding to the CA125 binding region of mesothelin find use in the treatment and prevention of cancers mediated by mesothelin-CA125 binding and/or cancers with tumor cells that overexpress mesothelin. Exemplary cancers include ovarian cancer, mesothelioma, non-small cell lung cancer, lung adenocarcinoma and pancreatic cancer.

With respect to therapeutic uses, the mesothelin peptide fragments can be administered to an individual with a demonstrated tumor burden or a diagnosis from a qualified clinician of having a cancer mediated by mesothelin-CA125 binding and/or a cancer with tumor cells that overexpress mesothelin (i.e., in comparison to a normal cell of the same tissue type). A therapeutically effective amount of the mesothelin peptide fragment corresponding to the CA125 binding region of mesothelin is administered to, e.g., reduce tumor burden, inhibit tumor growth or progression, and inhibit or prevent metastasis or migration by a measurable amount according to any method known in the art, e.g., by at least about 10%, 20%, 30%, 50%, 80% or 100%. Preferably, the measurable amount is therapeutically relevant or statistically significant.

With respect to prophylactic or preventative uses, the mesothelin peptide fragments can be administered to an individual, e.g., with a predisposed risk (e.g, environmental or genetic) to developing a cancer mediated by mesothelin-CA125 binding or mesothelin overexpression, with a surgically reduced tumor burden and/or in a remission from a cancer mediated by mesothelin-CA125 binding and/or a cancer with tumor cells that overexpress mesothelin. An effective amount of the mesothelin peptide fragment corresponding to the CA125 binding region of mesothelin is administered to, e.g., inhibit tumor growth, recurrence or progression, and inhibit or prevent metastasis or migration of tumor cells by a measurable amount according to any method known in the art. Preferably, the measurable amount is therapeutically relevant or statistically significant.

Administration of the mesothelin peptide fragments can be performed concurrently with currently practiced therapies and preventative strategies for cancers mediated by mesothelin-CA125 binding and/or cancers with tumor cells that overexpress mesothelin. For example, the mesothelin peptide fragments can be administered while the patient is undergoing chemotherapy or radiation therapy, or in coordination with surgical therapies.

b. Direct Inhibition of CA125-Mesothelin Binding

Mesothelin peptide fragments corresponding to the binding site of CA125 on mesothelin find use in disrupting the binding interaction of CA125 to mesothelin, in vitro and in vivo. Mesothelin peptide fragments of use in directly disrupting the binding of CA125 to mesothelin have an N-terminus beginning at about mesothelin amino acid residue 296 and a C-terminus ending in the range of mesothelin amino acid residue 359 to 390, although the directly blocking mesothelin fragments may by longer or shorter, e.g., by 1, 2, 3, 4, 5, 6, 7, 8, 9 or 10 amino acids. In some embodiments, the blocking mesothelin fragment is no longer than (i.e., in terms of the number of residues) mesothelin amino acid residues 296-359.

For carrying out methods of directly blocking the binding of CA125 to mesothelin with a mesothelin peptide fragment of the invention, an amount of peptide fragment sufficient to inhibit CA125/mesothelin binding, e.g., by at least about 25%, 50%, 75% or 100%, is administered to the site of CA125/mesothelin binding, e.g., intraperitoneally, intrathecally, intratumorally.

Mesothelin peptide fragments delivered to the site of CA125/mesothelin binding can be used to deliver an effector molecule, e.g., a drug, a radionuclide, a cytotoxin, a cytokine, a chemokine, as described above. In some embodiments, the blocking mesothelin peptide fragment is linked to a second polypeptide, as described herein. In some embodiments, the blocking mesothelin peptide fragment is fused to an Fc portion of an antibody.

c. Active Immunization to Induce Antibodies Against Mesothelin

Mesothelin peptide fragments corresponding to the binding site of CA125 on mesothelin find use in inducing an immune response in a host that produces antibodies that disrupt the binding interaction of CA125 to mesothelin. Mesothelin peptide fragments of use in directly disrupting the binding of CA125 have one or more immunogenic epitopes within amino acid residues 296-390 of mesothelin. In some embodiments, the blocking mesothelin fragment comprises one or more immunogenic epitopes within mesothelin amino acid residues 296-359. Immunogenic subfragments of about 7-9 contiguous amino acids in length within mesothelin fragments 296-359 or 296-390 can be used in immunization protocols to elicit antibodies that specifically bind to the CA 125 binding region of mesothelin and thereby interfere with CA125 binding to mesothelin. In some embodiments, the full length of mesothelin peptide fragment 296-359 or 296-390 is administered. In some embodiments, a polynucleotide encoding the mesothelin peptide fragment is administered.

For carrying out methods of actively immunizing with a mesothelin peptide fragment of the invention, an amount of peptide fragment sufficient to induce antibodies against the CA125 binding site of mesothelin is administered via a known route for vaccination, e.g., intradermally, subcutaneously, intramuscularly or intranasally.

d. Treatment Regimes

In general, treatment regimes for blocking mesothelin/CA125 interaction or for inducing an immune response against mesothelin involve administering a fragment of mesothelin corresponding to the CA 125 binding region of mesothelin as described herein, e.g., residues 296-390, and particularly residues 296-359 of mesothelin, to a patient. In prophylactic applications, pharmaceutical compositions or medicaments are administered to a patient susceptible to, or otherwise at risk of, developing a cancer mediated by mesothelin/CA125 interaction in an amount sufficient to eliminate or reduce the risk, lessen the severity, or delay the onset of the disease, including physiological, biochemical, histologic and/or behavioral symptoms of the disease, its complications and intermediate pathological phenotypes presenting during development of the disease.

In therapeutic applications, the mesothelin peptide fragments of the invention are administered to a patient suspected of, or already suffering from a cancer mediated by mesothelin/CA125 interaction in a regime comprising an amount and frequency of administration of the agent sufficient to cure, or at least partially arrest, or inhibit deterioration of the symptoms of the disease (physiological, biochemical, histologic and/or behavioral), including its complications and intermediate pathological phenotypes in development of the disease. In some methods, administration of agent reduces or eliminates primary tumor growth and/or tumor metastasis.

An amount adequate to accomplish therapeutic or prophylactic treatment is defined as a therapeutically- or prophylactically-effective dose. A combination of amount and dosage frequency adequate to accomplish the therapeutic or prophylactic treatment is defined as a therapeutically- or prophylactically-effective regime. In both prophylactic and therapeutic regimes, agents are usually administered in several dosages, starting low and incrementally increasing, until a sufficient immune response has been achieved with minimal or no adverse side effects. A dosage and frequency of administrations adequate to accomplish therapeutic or prophylactic treatment is defined as a therapeutically- or prophylactically-effective regime. Typically, the patient's immune response is monitored and repeated dosages are given if the immune response starts to wane. The immune response can be monitored, e.g., by detecting antibodies to mesothelin in the blood in the patient.

Effective doses of the agents and compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of peptide fragment administered depends on whether adjuvant is also administered, with higher dosages being required in the absence of adjuvant. The amount of peptide fragment for administration sometimes varies from 1-500 us per patient and more usually from 5-500 μg per injection for human administration. Occasionally, a higher dose of 1-2 mg per injection is used. Typically at least 10, 20, 50 or 100 μg is used for each human injection. For peptides used as vaccines, the mass of peptide fragment also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. Peptides used as blocking agents generally will be administered at higher doses, and more often, but over a shorter period of time in comparison to peptides used as vaccinating agents. On any given day that a dosage of peptide fragment is given, the dosage is greater than 1 μg/patient and usually greater than 10 μg/patient if adjuvant is also administered, and greater than 10 μg/patient and usually greater than 100 μg/patient in the absence of adjuvant.

For the purposes of vaccination with a mesothelin peptide fragment, a typical regimen involves an immunization injection followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Agents for blocking mesothelin/CA125 binding or inducing an immune response can be administered by parenteral, topical, intravenous, oral, subcutaneous, intraarterial, intracranial, intratumoral, intraperitoneal, intranasal or intramuscular means for prophylactic and/or therapeutic treatment. The most typical route of administration of an immunogenic agent for inducing an immune response is subcutaneous or intradermal although other routes can be equally effective. The next most common route is intramuscular injection. This type of injection is most typically performed in the arm or leg muscles. In some methods, blocking methothelin peptides are injected directly into a particular tissue or area where tumors are present or into the tumor itself, e.g., intraperitoneally or intratumorally.

e. Methods of Monitoring

The invention provides methods of detecting inhibition of mesothelin-CA125 binding in a patient suffering from or susceptible to a cancer mediated by mesothelin-CA125 cell adhesion. The methods are particularly useful for monitoring a course of treatment being administered to a patient. The methods can be used to monitor both therapeutic treatment on symptomatic patients and prophylactic treatment on asymptomatic patients.

The monitoring methods entail determining a baseline value of an antibody response or tumor burden in a patient before administering a dosage of a mesothelin peptide fragment, and comparing this with a value for the immune response or tumor burden after treatment, respectively.

With respect to vaccination therapies, a significant increase (i.e., greater than the typical margin of experimental error in repeat measurements of the same sample, expressed as one standard deviation from the mean of such measurements) in value of the antibody response signals a positive treatment outcome (i.e., that administration of the mesothelin peptide fragments has achieved or augmented an immune response). If the value for the antibody response does not change significantly, or decreases, a negative treatment outcome is indicated. In general, patients undergoing an initial course of treatment with an immunogenic agent are expected to show an increase in antibody response with successive dosages, which eventually reaches a plateau. Administration of agent is generally continued while the antibody response is increasing. Attainment of the plateau is an indicator that the administered of treatment can be discontinued or reduced in dosage or frequency.

With respect to therapies using the mesothelin fragments to directly block mesothelin-CA125 interaction, a significant decrease (i.e., greater than the typical margin of experimental error in repeat measurements of the same sample, expressed as one standard deviation from the mean of such measurements) in value of the tumor burden signals a positive treatment outcome (i.e., that administration of the mesothelin peptide fragments has blocked progression of tumor growth and/or metastasis).

In other methods, a control value (i.e., a mean and standard deviation) of an antibody response is determined for a control population. Typically the individuals in the control population have not received prior treatment. Measured values of the antibody response or tumor burden in a patient after administering a therapeutic agent are then compared with the control value. With respect to vaccination therapies, a significant increase in anti-mesothelin antibody response relative to the control value (e.g., greater than one standard deviation from the mean) signals a positive treatment outcome. A lack of significant increase or a decrease signals a negative treatment outcome. With respect to direct blocking therapies, a significant decrease in tumor burden relative to the control value (e.g., greater than one standard deviation from the mean) signals a positive treatment outcome. A lack of significant decrease or an increase signals a negative treatment outcome.

In other methods, a control value of antibody response or tumor burden (e.g., a mean and standard deviation) is determined from a control population of individuals who have undergone treatment with a mesothelin peptide fragment. Measured values of antibody response or tumor burden in a patient are compared with the control value. If the measured level in a patient is not significantly different (e.g., more than one standard deviation) from the control value, treatment can be discontinued. If the antibody response level in a patient is significantly below the control value, continued administration of agent is warranted. If the tumor burden level in a patient is significantly above the control value, continued administration of agent is warranted.

In other methods, a patient who is not presently receiving treatment but has undergone a previous course of treatment is monitored for antibody response or tumor burden to determine whether a resumption of treatment is required. The measured value of antibody response or tumor burden in the patient can be compared with a value of antibody response or tumor burden previously achieved in the patient after a previous course of treatment. A significant decrease in antibody response or increase in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease in antibody response or increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can analyzed for indication of neoplasia or an immune response to mesothelin, particularly the CA125 binding region of mesothelin. The immune response can be determined from the presence of antibodies that specifically bind to mesothelin. Antibodies can be detected in a binding assay to a ligand that specifically binds to the antibodies. Typically the ligand is immobilized. Binding can be detected using a labeled anti-idiotypic antibody. Neoplasia or tumor burden can be detected using any method known in the art, e.g., visual observation of a biopsy by a qualified pathologist, or other visualization techniques, e.g., radiography, ultrasound, magnetic resonance imaging (MRI).

EXAMPLES

The following examples are offered to illustrate, but not to limit the claimed invention.

Experimental Procedures

Cell Culture—

OVCAR-3 (ovarian) cells were grown in RPMI 1640 (Dulbecco) supplemented with 20% FBS, 1% penicillin-streptomycin, 1% L-Glutamine, and 0.2% human insulin. YOU (mesothelioma) cells were grown in RPMI 1640 (Dulbecco) supplemented with 10% FBS, 1% penicillin-streptomycin, and 1% L-Glutamine. HEK 293T cells were grown in 100 mm tissue culture dishes (Falcon) with Dulbecco's Modified Eagle Medium (DMEM) and supplemented with 10% FBS, 1% penicillin-streptomycin, and 1% L-glutamine.

Truncated Mutant Constructs—

Full-length and fragments of mesothelin were amplified by PCR from pMH107 (GenBank Accession No. AY743922) (Ho, et al., (2005) *J. Biol. Chem.* 280, 607-617). Primers were designed to incorporate flanking EcoRI and NotI restriction enzyme sites to facilitate in-frame cloning into a modified pSecTag2 vector (Invitrogen) (Table 1). Constructs contained an Ig-κ leader sequence followed by the rabbit IgG Fc and the full-length sequence of extracellular domain of mesothelin (pMH113) or its fragments, followed by a myc epitope and His tag. The rabbit IgG Fc (rFc) and mesothelin fragments were separated by a thrombin cleavage site and a flexible linker. The rFc-mouse mesothelin fusion (pMH117) was constructed using the same strategy.

TABLE 1

Primers used to construct truncated mutants of mesothelin.

| Fragments | Primers (5' -> 3') | SEQ ID NO: |
|---|---|---|
| Region I | Forward: AGAAGAAGAGAATTCGAAGTGGAGAAGACAGCCTGT | 11 |
| (296-390)* | Reverse: CTCTTCTTCTGCGGCCGCCGTCACATTCCACTTGCGAAT | 12 |
| Region II | Forward: AGAAGAAGAGAATTCTCCCTGGAGACCCTGAAGGCT | 13 |
| (391-486) | Reverse: CTCTTCTTCTGCGGCCGCCTGGAAAGCAAGGCGGGCCTT | 14 |
| Region III | Forward: AGAAGAAGAGAATTCAACATGAACGGGTCCGAATAC | 15 |
| (487-581) | Reverse: CTCTTCTTCTGCGGCCGCGCCCTGTAGCCCCAGCCCCAG | 16 |
| Region IAB | Forward: AGAAGAAGAGAATTCGAAGTGGAGAAGACAGCCTGT | 17 |
| (296-359) | Reverse: CTCTTCTTCTGCGGCCGCGAGCTCATCCAGTTTATGCTT | 18 |
| Region IBC | Forward: AGAAGAAGAGAATTCGATGCGGCCCTGCTGGCCACC | 19 |
| (328-405) | Reverse: CTCTTCTTCTGCGGCCGCGTGCCCTTTGTTGACTTCAAG | 20 |
| Region IA | Forward: AGAAGAAGAAAGCTTGAAGTGGAGAAGACAGCCTGT | 21 |
| (296-337) | Reverse: TCTTCTTCTGGATCCGTCCATCTGGGTGGCCAGCAG | 22 |
| Region IB | Forward: AGAAGAAGAGAATTCGATGCGGCCCTGCTGGCCACC | 23 |
| (328-369) | Reverse: CTCTTCTTCTGCGGCCGCGATCACAGACTCGGGGTAACC | 24 |
| Region IC | Forward: AGAAGAAGAGAATTCTACCCACAAGGTTACCCCGAG | 25 |
| (360-405) | Reverse: CTCTTCTTCTGCGGCCGCGTGCCCTTTGTTGACTTCAAG | 26 |

*The restriction enzyme sites are underlined.

Alanine mutants were generated by PCR mutagenesis of pMH107-derived human mesothelin cDNA followed by cloning into the modified pSecTag2 vector. Mutations were introduced in either forward or reverse primers or by using a two-step overlap-extension PCR reaction (Table 2).

TABLE 2

Primers used to generate alanine replacement mutants of mesothelin.

| Mutants | Primers (5' -> 3') | SEQ ID NO: |
|---|---|---|
| Y318A | Forward: AGAAGAGAATTCGAAGTGGAGAAGACAGCCTGTCCTTCAGGCAAGAAGGCCCGCGAGATAGACGAGAGCCTCATCTTCGCCAAGAAGTGGGAG | 27 |
| | Reverse: CTCTTCTTCTGCGGCCGCGAGCTCATCCAGTTTATGCTT | 28 |
| W321A | Forward: TCATCTTCTACAAGAAGGCGGAGCTGGAAGCCTGCGTGG | 29 |
| | Reverse: CCACGCAGGCTTCCAGCTCCGCCTTCTTGTAGAAGATGA | 30 |

TABLE 2-continued

Primers used to generate alanine replacement mutants of mesothelin.

| Mutants | Primers (5' -> 3') | SEQ ID NO: |
|---|---|---|
| E324A | Forward: AGAAGAGAATTCGAAGTGGAGAAGACAGCCTGTCCTTCAGGCAAGAAGGCCCGCGAGATAGACGAGAGCCTCATCTTCTACAAGAAGTGGGAGCTGGCAGCCTGCGTG | 31 |
| | Reverse: CTCTTCTTCTGCGGCCGCGAGCTCATCCAGTTTATGCTT | 32 |
| F344A | Forward: AGAAGAAGAGAATTCGAAGTGGAGAAGACAGCCTGT | 33 |
| | Reverse: TTCTTCTGCGGCCGCGAGCTCATCCAGTTTATGCTTTAGGACGTCCAGCTGCTCGTAGGT GGCGGGGATGGCGTT | 34 |
| E347A | Forward: AGAAGAAGAGAATTCGAAGTGGAGAAGACAGCCTGT | 35 |
| | Reverse: TTCTTCTGCGGCCGCGAGCTCATCCAGTTTATGCTTTAGGACGTCCAGCTGCGCGTAGGTGAAGGG | 36 |
| K353A | Forward: AGAAGAAGAGAATTCGAAGTGGAGAAGACAGCCTGT | 37 |
| | Reverse: TTCTTCTGCGGCCGCGAGCTCATCCAGTTTATGCGCTAGGACGTCCAG | 38 |
| H354A | Forward: AGAAGAAGAGAATTCGAAGTGGAGAAGACAGCCTGT | 39 |
| | Reverse: CTCTTCTTCTGCGGCCGCGAGCTCATCCAGTTTAGCCTTTAGGACGTC | 40 |
| K355A | Forward: AGAAGAAGAGAATTCGAAGTGGAGAAGACAGCCTGT | 41 |
| | Revere: CTCTTCTTCTGCGGCCGCGAGCTCATCCAGTGCATGCTTTAGGACGTC | 42 |

*The restriction enzyme sites are underlined.

Transfections and mesothelin mutant-Fc fusion protein production—HEK 293T cells were grown until 60% confluent on 100 mm tissue culture dishes (Falcon). Constructs encoding mesothelin-Fc fusion proteins were transiently transfected using Lipofectamine (Invitrogen) in 6 mL serum free media. Three to 5 h later, 6 mL of 20% FBS DMEM was added to each dish and incubated for 48 h. Media was harvested subsequently on a daily basis and replaced with fresh medium. Fc fusion proteins were purified from the media using columns containing Protein A Sepharose (Amersham Biosciences). One mL columns were loaded, washed with citrate-phosphate buffer pH 5.0, and eluted with 100 mM glycine-HCl pH 3.0. Fractions were collected using the AKTA FPLC system (GE Life Sciences) and pooled and concentrated. Final protein concentration was measured using Coomassie Plus Protein Assay Reagent (Pierce). Fractions of the dominant peak were run on a SDS-PAGE gel under non-reducing and reducing conditions. Mesothelin and its mutants were over a TSK size exclusion column to verify that the generated proteins were not aggregated.

Flow Cytometry—

To determine binding of mesothelin fragments to CA125 on the cell surface, OVCAR-3 or YOU cells were grown until confluent, detached, and then incubated with 1 μg/mL of mesothelin or its fragments in FACS buffer (5% BSA, 0.01% $NaN_3$) for 1 h on ice. Bound fragments were detected by incubating with a 1:200 dilution of Goat anti-Rabbit IgG-PE (Biosource) secondary antibody in FACS buffer for 0.5 h on ice. Cells were analyzed using FACSCalibur (BD Biosciences). Each binding experiment was repeated three to five times.

In inhibition assays, cells were incubated with Flag-tagged mesothelin and excess amount (10 folds) of mesothelin or mesothelin fragments without a Flag tag for 1 h on ice. Bound Flag-tagged mesothelin proteins were detected by incubating with 1:100 dilution of an anti-Flag tag mAb (Sigma) followed by PE conjugated goat anti-mouse IgG (Biosource).

Sandwich ELISA—

Nunc MaxiSorp 96 well flat-bottomed plates were incubated overnight with 5 μg/mL, goat anti-rabbit IgG (Jackson ImmunoResearch Laboratories) in PBS, followed by an overnight block with 5% BSA, 0.01% $NaN_3$ in PBS. Purified Fc mesothelin fragments were diluted to 1 μg/mL in ELISA buffer (0.01% Tween 20, 10% Pierce SuperBlock) and incubated on plate for 1 h at room temperature (RT). Plates were then incubated with OVCAR-3 supernatant containing CA125 for 1 h at RT. To detect bound CA125 a 1:200 dilution of anti-CA125 OC125 mAb (Zymed) was incubated for an additional hour at RT; subsequently a 1:1500 dilution of goat anti-mouse IgG HRP conjugate (Biosource) was added for 1 h at RT. The plates were washed four times with ELISA buffer between each coating. Visualization was achieved with TMB detection reagent (KPL) and absorbance was read at 450 nm with SpectraMax Plus plate reader (Molecular Devices).

Western Blots—

Purified Fc mesothelin fragments (500 ng) were mixed with Laemmli Sample Buffer (Biorad) supplemented with 5% B-Mercaptoethanol. Samples were boiled for 2 min and separated on 4-20% SDS-PAGE gels (Invitrogen). After transfer for 4 h at 30V, the PVDF membrane was blocked overnight at 4° C. in 1% Western Blocking Reagent (Roche)

in Tris buffered saline (50 mM Tris-HCl, 150 mM NaCl). The membrane was then incubated with OVCAR-3 supernatant+0.5% blocking solution for 1 h at RT. This was followed by incubation with 1:200 dilution of OC125 mAb for 1 h at RT. Detection was performed with goat anti-mouse IgG-HRP conjugate (Biosource) 1:1000 for 1 h.

Determination of Affinity Constants (KD)—

As previously described (Ho, et al., (2005) *J. Biol. Chem.* 280, 607-617), equilibrium constants and Scatchard plots were determined by using the Marquardt-Levenberg algorithm for nonlinear regression with the Prism software (version 5.0, GraphPad Software, San Diego, Calif.).

Statistical Analysis—

The data obtained was entered in Prism (version 5) for Windows (GraphPad Software) for statistical analysis. Flow cytometry raw data were analyzed by ANOVA with Dunnett's and Newman-Keuls multiple comparison post tests. Ps<0.05 were considered statistically significant.

Results

Generation of Mesothelin Mutants—

Truncated mutants of mesothelin were generated to sequentially narrow down the binding domain to CA125. As shown in FIG. 1, portions of mesothelin were PCR amplified to incorporate NotI and EcoRI restriction sites and cloned into a modified pSecTag 2B vector containing an N-terminal rFc fragment. HEK 293T cells were transfected and Fc mesothelin proteins were collected and purified from the supernatant over the course of 8-10 days. Constructs encoding amino acid residues 296-390 (Region I), 391-486 (Region II), and 487-581 (Region III) of mesothelin were initially generated and tested. Constructs encoding smaller fragments within Region I, Region IAB (296-359), Region IBC (328-405), Region IA (296-337), Region IB (328-369), and Region IC (360-405) were also generated. It was found that secretion of the IA (296-337) fragment was prevented by protein aggregation; however, this problem was circumvented by moving the rFc to the C-terminus of the mesothelin fragment.

Figure 2:
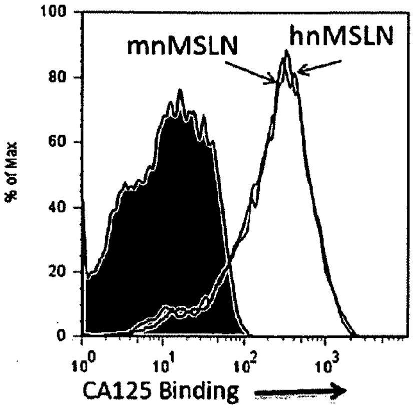
FIGS. 2A-B. Key residues proposed for alanine mutations. A. OVCAR-3 cells were incubated with 1 mg/mL of human mesothelin (hnMSLN) or mouse mesothelin (mnMSLN) rFc fusion proteins. The mesothelin binding on OVCAR-3 cells was detected by a goat anti-rabbit IgG Fc PE conjugate. B. Eight residues identical between hnMSLN (SEQ ID NO:7) and mnMSLN (SEQ ID NO:8) in Region IAB were selected for alanine replacement. Region IAB starts at E296 and ends at L359 (*) in hnMSLN. Alanine mutants within Region IAB (296-359) were expressed. Alanine mutants Y318A, W321A, E324A and H354A (arrows) were secreted and purified for analysis. The other four mutants, F344A, E347A, K353A and K355A, were not secreted and found aggregated inside transfected HEK 293T cells. Consensus=SEQ ID NO:9.
Figure 2:
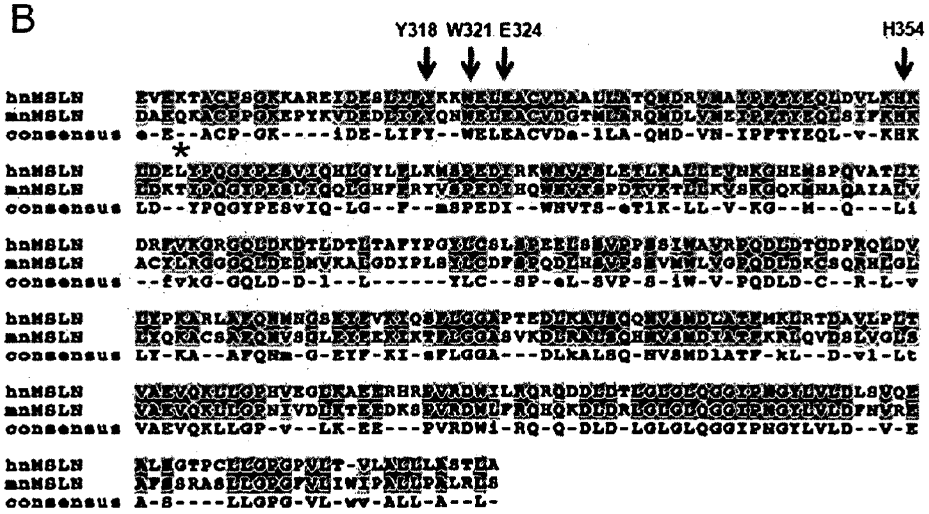
Figure 3:
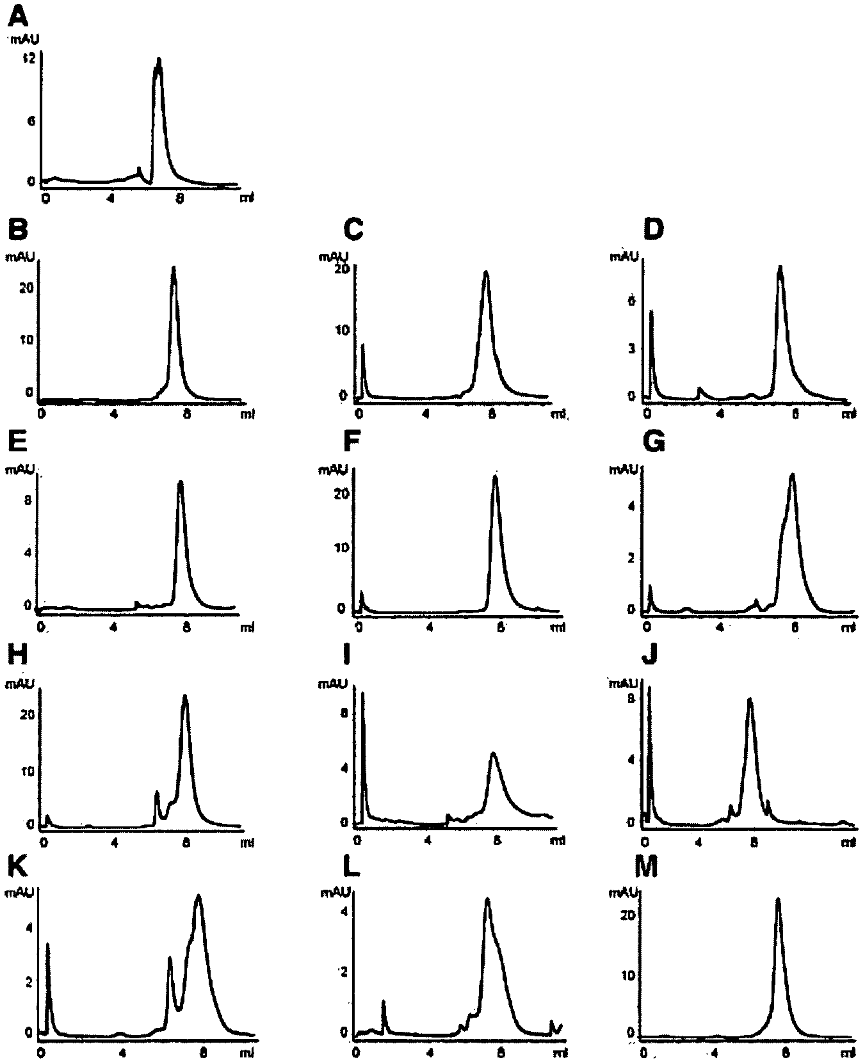
FIGS. 3A-M. Chromatograms from TSK size exclusion columns. Purified mesothelin (A) and truncated mutants of mesothelin (B-I) and alanine mutants within Region IAB (J-K) were run over a TSK size exclusion column to verify that the generated proteins were not aggregated. Truncated mutants and alanine mutants had a dominant peak that matched with the wild-type fragment, indicating that there was minimal aggregation. A. Full-length mature MSLN 296-581; B. Region 1296-390; C. Region II 391-486; D. Region III 487-581; E. Region IAB 296-359; F. Region IBC 328-405; G. Region IA 296-337; H. Region IB 328-369; I. Region IC 360-405; J. Y318A; K. W321A; L. E324A; and M. H354A.

PCR mutagenesis was used to generate a panel of alanine mutants within region 296-359 (Region IAB). As shown in FIG. 2A, both human and mouse mesothelin proteins bind human CA125. It was reasoned that those residues conserved between the two species would be more likely to be involved in the interaction. Specific amino acids were targeted based on the homology between human and murine mesothelin (FIG. 2B). In addition, we hypothesized that these residues are likely to be involved in the carbohydrate binding. In total, eight alanine mutant constructs were made: Y318A, W321A, E324A, F344A, E347A, K353A, H354A, and K355A. Of these mutants, four were secreted at high enough levels to purify using a Protein A column—Y318A, W321A, E324A, and H354A. The purity and molecular weight of each purified protein was confirmed on SDS-PAGE. The other four mutants, F344A, E347A, K353A and K355A, were not secreted into the culture supernatants due to aggregation inside cells according to immunoblotting of whole cell lysates, indicating that mutations of these residues may cause misfolding of mesothelin. For all proteins purified, a distinct peak was found on a TSK size exclusion column (FIG. 3). The rFc-extracellular portion of mesothelin 296-581 fusion protein (full-length) was estimated to be approximately 75-kDa, while truncated mutants were relatively smaller in molecular weight (~50-kDa for Regions I, II and III and ~40-kDa for IAB, IBC and alanine mutants of IAB).

Binding of CA125 to Mesothelin and its Mutants—

Figure 4:
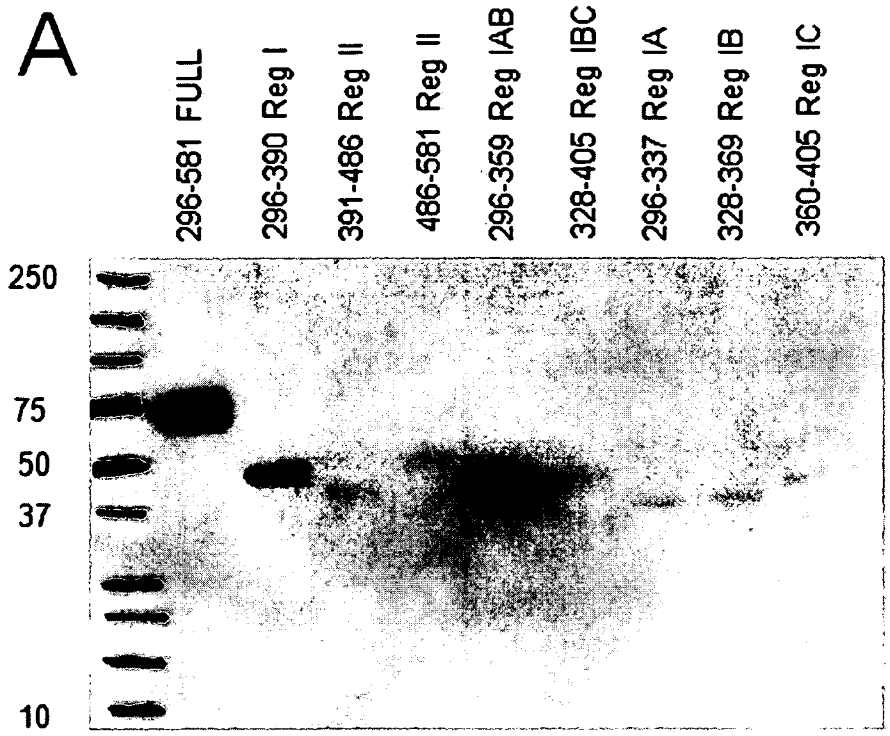
FIGS. 4A-B. Western blots of mesothelin fragments and alanine mutants. Each protein (500 ng) was run on an SDS-PAGE gel and transferred to a PVDF membrane. Membrane was blotted with OVCAR-3 supernatant containing CA125 followed by OC125 (anti-CA125 mAb). A. Full-length extracellular domain of mesothelin (FULL, 296-581), Region I (296-390) and Region IAB (296-359) bind CA125. Regions II (391-486), III (487-581), IBC (327-390), IA (296-337), IB (328-369) and IC (360-405) do not bind CA125. B. Alanine mutants within Region IAB (296-359) show differential binding. Alanine mutations at Tyr-318 (Y318A) and Glu-324 (E324A) abolish the binding of mesothelin to CA125. Alanine mutation at Trp-321 (W321A) partially reduce the binding of mesothelin to CA125. The alanine mutation at His-354 does not change the mesothelin-CA125 interaction.
Figure 4:
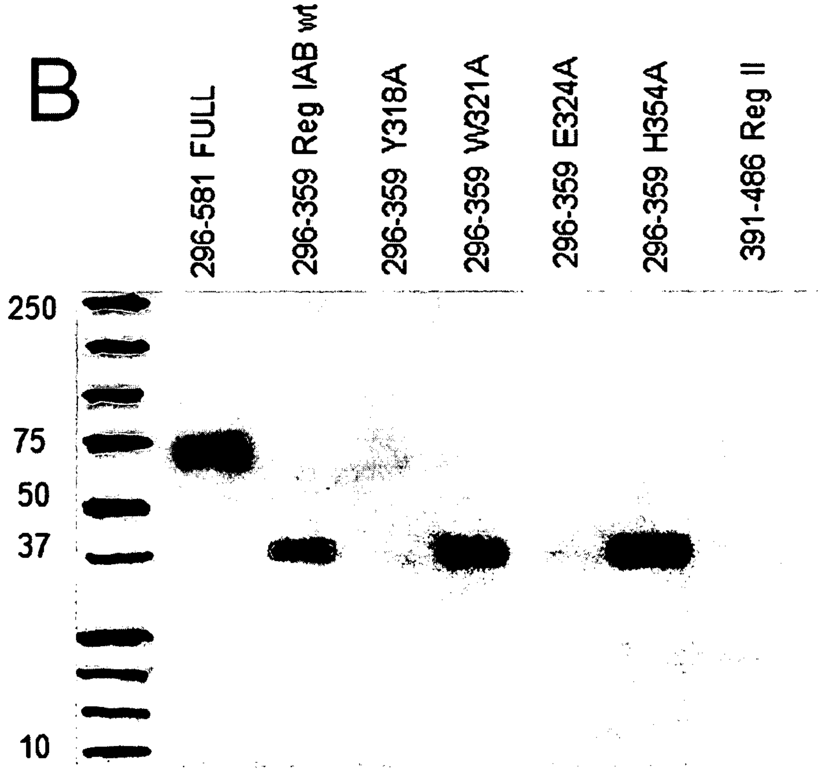

To examine the interaction of CA125 and mesothelin mutants, we used Western blot overlay analysis. We ran equal amounts (500 ng) of each protein an SDS-PAGE gel and transferred to a PVDF membrane. Membrane was blotted with OVCAR-3 supernatant containing CA125 followed by OC125, an anti-CA125 mAb. As shown in FIG. 4, full-length extracellular domain of mesothelin (296-581), Region I (296-390) and Region JAB (296-359) bound CA125. A 64 amino acid fragment (IAB) at the N-terminus of mesothelin (296-359) retained 100% binding capability to CA125. However, three smaller fragments, Region IA (296-337), Region IB (328-369), and Region IC (360-405), consisting of approximately 42 amino acids covering all the residues within Region I showed no binding to CA125 in Western blot. The alanine mutation at His-354 did not change the mesothelin-CA125 interaction. Interestingly, alanine mutations at Tyr-318 (Y318A) and Glu-324 (E324A) abolished the binding of mesothelin to CA125. Alanine mutation at Trp-321 (W321A) partially reduced the binding of mesothelin to CA125.

Kinetic Studies by ELISA—

Figure 5:
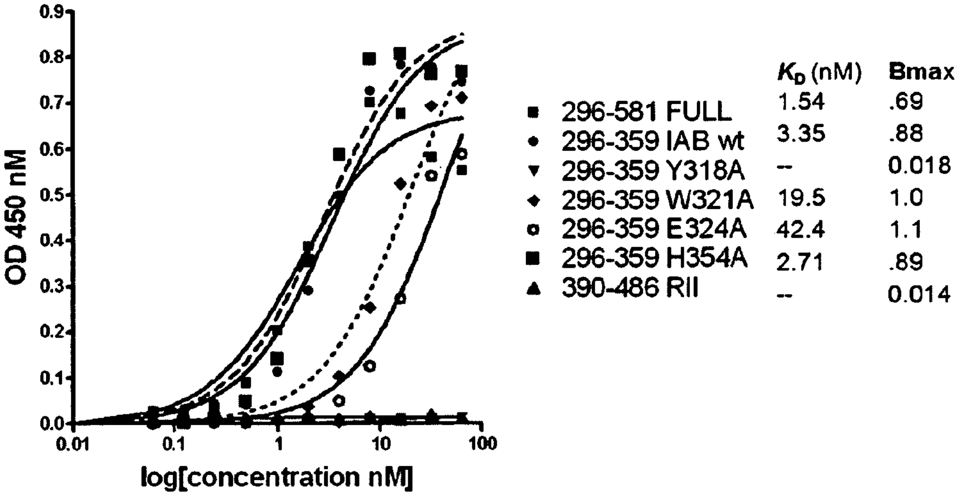
FIG. 5. Binding kinetics of mesothelin mutants and CA125. Scatchard plots (top left corner) were made. ELISA plates captured the Fc mesothelin mutant fusion proteins at various concentrations (x axis; see Experimental Procedures). OVCAR-3 supernatant containing soluble CA125 was then added, followed by the OC125 mAb and a goat anti-mouse IgG HRP. Visualization was achieved with TMB detection reagent and absorbance was read at 450 nm (y axis). The full-length mature form of mesothelin (FULL) bound to CA125 with an approximate affinity of 1.54 nM. Region IAB wild-type (wt) (296-359) had a KD of 3.35 nM. Substitution of the tyrosine at position 318 with an alanine (Y318A) completely disrupted the interaction with CA125. Alanine mutation at Glu-324 (E324A; KD=42.4 nM) and Trp-321 (W321A; KD=19.5 nM) reduce the binding of mesothelin to CA125. The alanine mutation at His-354 (H354A) does not change the mesothelin-CA125 interaction (KD=2.71 nM).

To precisely characterize the interaction between CA125 and mesothelin and to determine a binding affinity (KD) for each mesothelin fragment, we used a quantitative ELISA-based assay. ELISA plates were coated with a goat anti-rabbit IgG antibody overnight for capturing the Fc mesothelin mutant fusion proteins. OVCAR-3 supernatant containing soluble CA125 was then added, followed by the OC125 mAb. Overall results from the ELISA were consistent with those seen in the Western blot overlay assays except for the E324A mutant of mesothelin (FIG. 5). The average KD for the binding of the Fc fusion protein of wild-type mature mesothelin (296-598), Region I (296-390) and JAB (296-359) to CA125 was ~3 nM. The KD for the mesothelin-CA125 interaction is consistent with the value (~5 nM) previously obtained on OVCAR-3 cells by flow cytometry (Gubbels, et al., (2006) *Mol. Cancer* 5, 50). Three smaller fragments (296-337, 328-369, 360-405) within Region I showed no binding to CA125 in ELISA (data not shown), indicating the first 64 residues at the N-terminus of cell surface mesothelin is the irreducible binding domain on mesothelin for the CA 125 protein. It is striking that substitution of the tyrosine at position 318 with an alanine (Y318A) completely disrupted the interaction with CA125. Alanine mutations at Glu-324 (E324A; KD=42.4 nM) and Trp-321 (W321A; KD=19.5 nM) partially reduced the binding of mesothelin to CA125. The alanine mutation at His-354 (H354A) did not change the mesothelin-CA125 interaction (KD=2.71 nM).

To verify that fragments were specifically binding to CA 125, an ELISA assay was employed wherein captured mesothelin fragments were incubated with either OVCAR-3 supernatant containing CA125 or supernatant from the OVCAR-3 with knockdown of CA125 expression. No signal was detected from those fragments incubated with the supernatant from CA125-knockdown cells (data not shown), indicating that the binding between mesothelin and CA125 in ELISA was specific.

Cell Binding Assays by Flow Cytometry—

Figure 6:
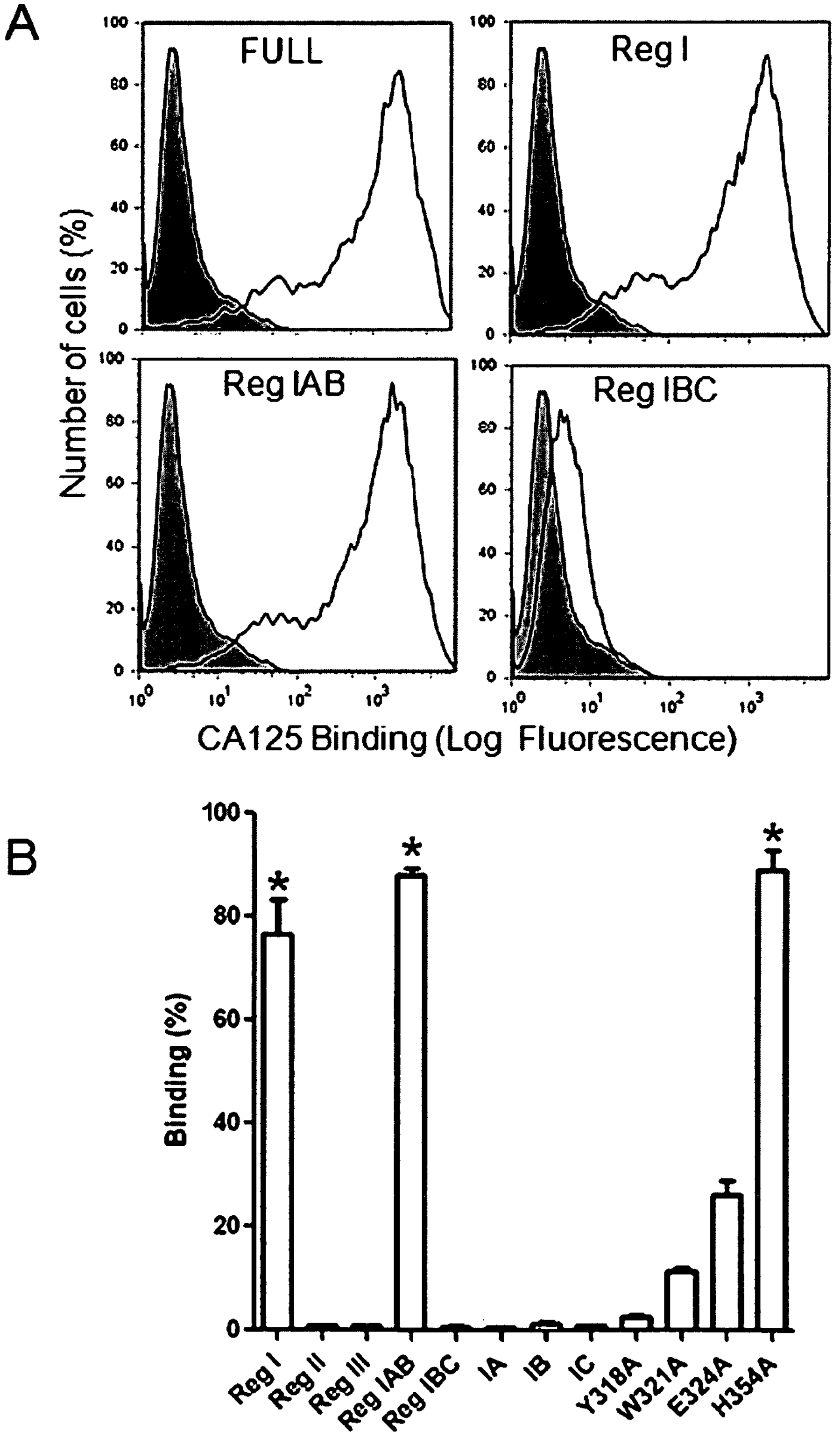
FIGS. 6A-B. Binding of truncated mutants and alanine mutants to CA125 on the cell surface of OVCAR-3 cells. A. OVCAR-3 ovarian cancer cells were incubated with full-length extracellular domain of mesothelin (FULL), Region I, IAB or IBC. The binding was visualized with a goat anti-rabbit IgG PE-conjugated secondary antibody by flow cytometry (gray line). Light gray shaded plot: secondary antibody only. B. A fluorescence intensity (geometrical mean) was used to quantitatively measure the CA125 binding. In each experiment, the binding of the full-length mature form of mesothelin (FULL) to CA125 was determined as 100% of binding. The secondary antibody only was used as a negative (0%) control. Full-length extracellular domain of mesothelin (296-581), Region I (296-390), Region IAB (296-359) and the H354A mutant of IAB bound to CA125 on OVCAR-3 cells significantly stronger than any other fragments or mutants on the figure (*$p<0.05$).

To assess binding to CA125 on cancer cells, wild-type mesothelin and its mutants were incubated with cells. As shown in FIG. 6, Region I (a 95 amino acid fragment consisting of residues 296-390 at the N-terminus) of mesothelin was found to bind to OVCAR-3 cells, while fragments Region II (391-486) and Region III (487-581) showed no binding. The smallest fragment that still contained most (~90%) of binding activity to CA125 was Region IAB. Three smaller fragments within Region I, Region IA (296-337), IB (328-369), and IC (360-405), were also tested. Only Region IB had a modest (~10%) CA125-binding activity. These data indicate that JAB, the first 64 residues at the N-terminus of cell surface mesothelin, is the minimum region which retains the most binding activity to CA125. The IAB binding domain was found to bind with comparable affinity, when compared to the full-length mesothelin (FULL). This suggests that it is primarily the N-terminus of cell surface mesothelin that is involved in the interaction with CA125 and the minimum sequence for CA125 binding activity is Region IAB (328-405).

Four alanine mutants (Y318A, W321A, E324A, and H354A) generated within the region 296-359 were similarly assessed for their ability to bind to CA125 on the surface of OVCAR-3 cells. It was found that the substitution of alanine for tyrosine at residue 318 completely ablated binding (FIG. 6). The H354A mutant conversely showed comparable binding to CA125 as the wild-type region 296-359. Alanine mutants of the tryptophan at 321 and glutamic acid at 324 also demonstrated decrease in binding (10-20%) to CA125 on the surface of OVCAR-3 cells.

Using ANOVA with Dunnett's and Newman-Keuls multiple comparison post tests, we have demonstrated that frill-length mesothelin (FULL), Region I, IAB and the H354A mutant significantly bound to CA125 on OVCAR-3 cells, as compared to Regions II, III, IBC, IA, IB, IC and the Y318A, W321A and E324A mutants ($p<0.05$). As compared to Region IAB, the binding by full-length mesothelin (FULL), the H354A mutant and Region I was not significant ($p>0.05$), indicating that IAB is the minimal sequence of CA125-binding domain.

Figure 7:
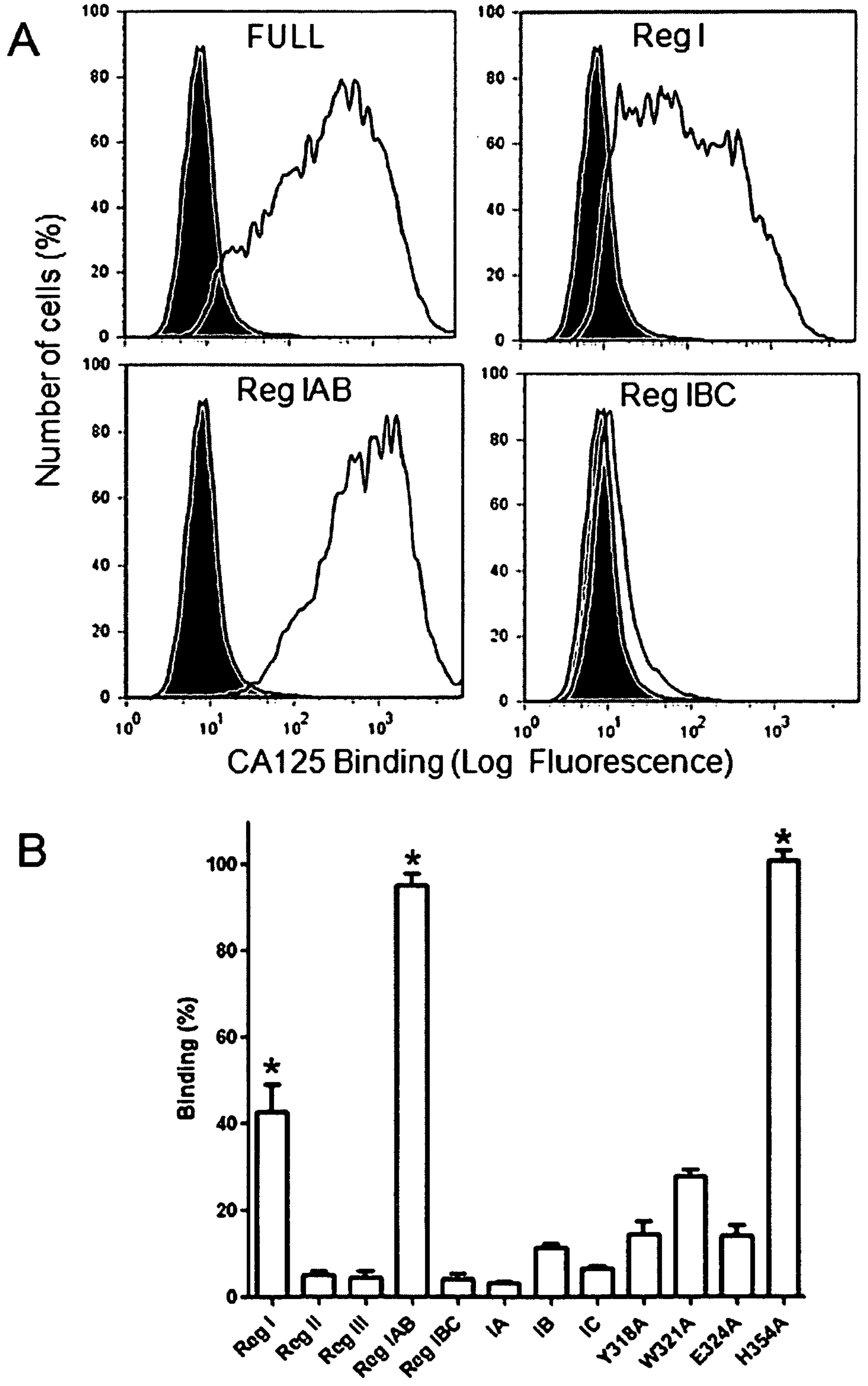
FIGS. 7A-B. Binding of truncated mutants and alanine mutants to CA125 on the cell surface of YOU cells. A. YOU mesothelioma cells were incubated with full-length extracellular domain of mesothelin (FULL) or a mutant of mesothelin. The binding was visualized with a goat anti-rabbit IgG PE-conjugated secondary antibody by flow cytometry (gray line). Light gray shaded plot: secondary antibody only. B. A mean fluorescence intensity (geometrical mean) was used to quantitatively measure the CA125 binding on YOU cells. In each experiment, the binding of the full-length mesothelin (FULL) to CA125 was determined as 100% of binding. The secondary antibody only was used as a negative (0%) control. Full-length extracellular domain of mesothelin (296-581), Region I (296-390), Region IAB (296-359) and the H354A mutant of IAB bound to CA125 on YOU cells significantly stronger than any other fragments or mutants on the figure (*$p<0.05$).
Figure 8:
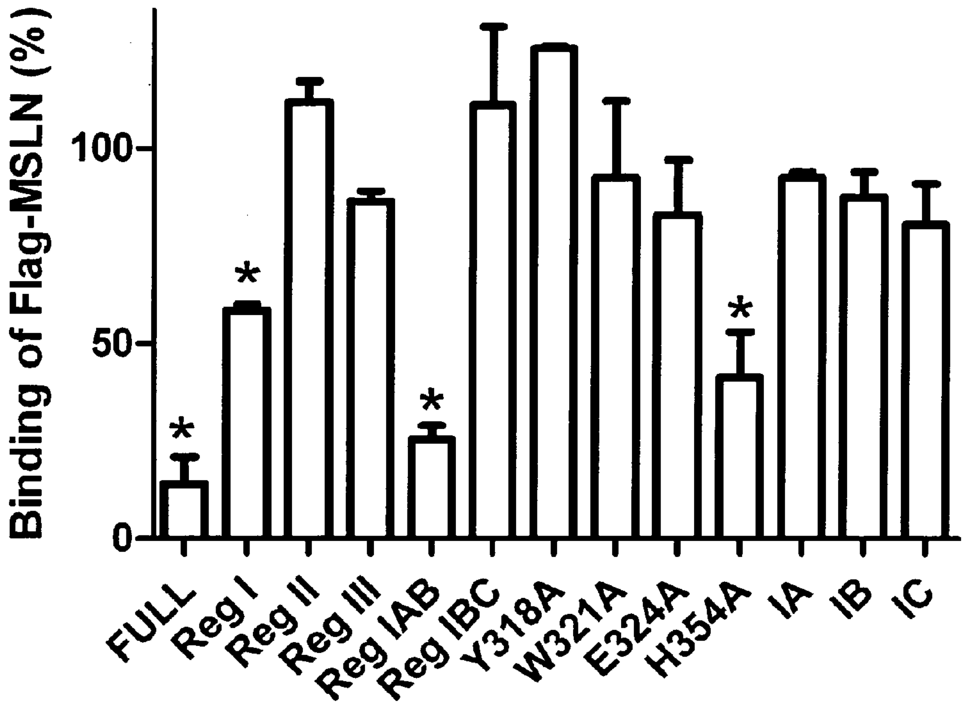
FIG. 8. Inhibition of the mesothelin-CA125 interaction by mesothelin mutants. OVCAR-3 cells were incubated with mesothelin or each mutant and the Flag-tagged mesothelin (see Experimental Procedures). The binding of Flag-mesothelin to CA125 was detected by an anti-Flag mAb. Full-length extracellular domain of mesothelin (296-581), Region I (296-390), CA125 binding domain or Region IAB (296-359) and the H354A mutant of IAB (dark gray shading) can significantly block the binding of Flag-tagged mesothelin to CA125 on OVCAR-3 cells (*$p<0.05$).

Since surface protein expression of mesothelin and CA125 are also found frequently in malignant mesothelioma, we then examined the binding of mesothelin and its mutants to the YOU mesothelioma cell line (FIG. 7). The binding patterns were similar to those seen in OVCAR-3 cells except for Region I. As shown in FIG. 8, wild-type mesothelin (FULL), Regions I and JAB bound CA125 on YOU cells significantly stronger than Regions II, III and IBC ($p<0.05$). Unlike what we saw in OVCAR-3 cells, Region I retained about 40% of the CA125 binding activity on YOU cells. Nevertheless, the binding of Region IAB to CA125 on YOU cells is comparable to the full-length mesothelin (FULL) ($p>0.05$). We also found that Region IB had a modest (~10%) binding activity. The alanine replacements at positions 318, 321 and 324 showed significant decrease of CA125 binding activities (10-30%) on YOU cells.

Inhibition of the Mesothelin-CA125 Interaction by the CA125-Binding Domain—

The molecular mechanisms underlying the cell adhesion and signaling induced by the mesothelin-CA125 interaction are not clear. An ideal antagonist drug would disrupt the mesothelin-CA125 interaction but not induce cell adhesion and signaling. To this end, we examined if any of the mesothelin truncated or alanine mutants reported here can compete with the binding of wild-type mesothelin to CA125. We co-incubated a Flag-tagged wild-type mesothelin with a panel of our mesothelin mutants (FIG. 8). Region JAB can effectively inhibit the mesothelin-CA125 interaction. Other constructs such as Region I and H354A can also inhibit the mesothelin-CA125 interaction while Regions II, III and IBC, mutants Y318A, E324A and W321A cannot. We have demonstrated that full-length mesothelin (FULL), Region I, IAB and the H354A mutant significantly inhibited the binding of mesothelin with a Flag tag to CA125 on OVCAR-3 cells, as compared to Regions II, III, IBC and the Y318A, W321A and E324A mutants ($p<0.05$). As compared to Region IAB, the inhibition of the methelin-CA125 interaction by full-length mesothelin (FULL) and Region I was not significant ($p>0.05$), clearly indicating that IAB is the minimal sequence (296-359) of CA125-binding domain.

Inhibition of Cancer Cell Adhesion by the CA125-Binding Domain—

Figure 9:
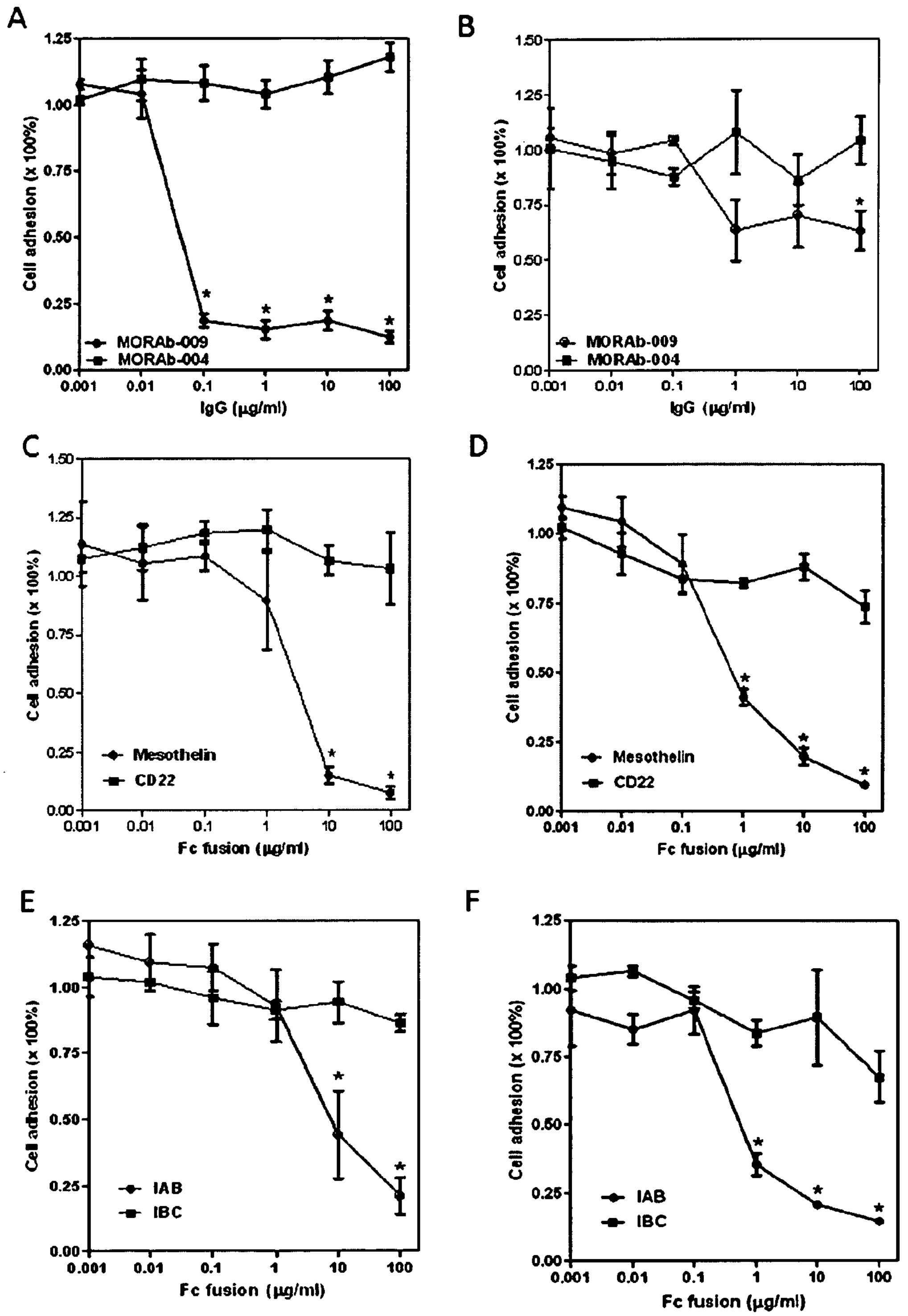
FIG. 9. The CA125-binding domain blocks the mesothelin/CA 125-mediated cancer cell adhesion. OVCAR-3 (A, C, E) or YOU cancer cells (B, D, F) formed monolayers. The OVCAR3 or YOU cancer cell monolayer was pre-incubated with MORAb-009 (an antibody to mesothelin), MORAb-004 (an irrelevant control antibody), full-length mesothelin, the CA125-binding domain (IAB), IBC (a mesothelin fragment) or CD22 Fc fusion proteins before fluorescently labeled mesothelin-expressing H9 cells were added. Mesothelin or IAB significantly blocked cancer cell adhesion with concentrations as low as 10 μg/mL on OVCAR3 cells (C, E) or 1 μg/mL on YOU cells (D, F) as compared to the control protein (CD22 or IBC)(*$p<0.05$).

We show herein that the CA125-binding domain can functionally block cancer cell adhesion. We used the assay system recently established by Hassan et al. (2007) *Cancer Immun.* 7:20. We measured adhesion of fluorescently labeled mesothelin-expressing H9 cells (Ho, et al., (2005) *Clin. Cancer Res.* 11, 3814-3820) onto CA125 positive OVCAR-3 or YOU cancer cells. FIG. 9 shows the results of this study. Significant heterotypic cell binding was seen on a monolayer of OVCAR-3 or YOU cells with the control CD22-Fc fusion protein or a control fragment (Region IBC). The CA125-binding domain (IAB)-Fc fusion protein completely abolished H9 cell adhesion onto OVCAR-3 or YOU cells. A statistically significant inhibition with the CA125-domain was detected with concentrations as low as 1 μg/mL (FIG. 9).

Structure of CA125-Binding Domain—

Figure 10:
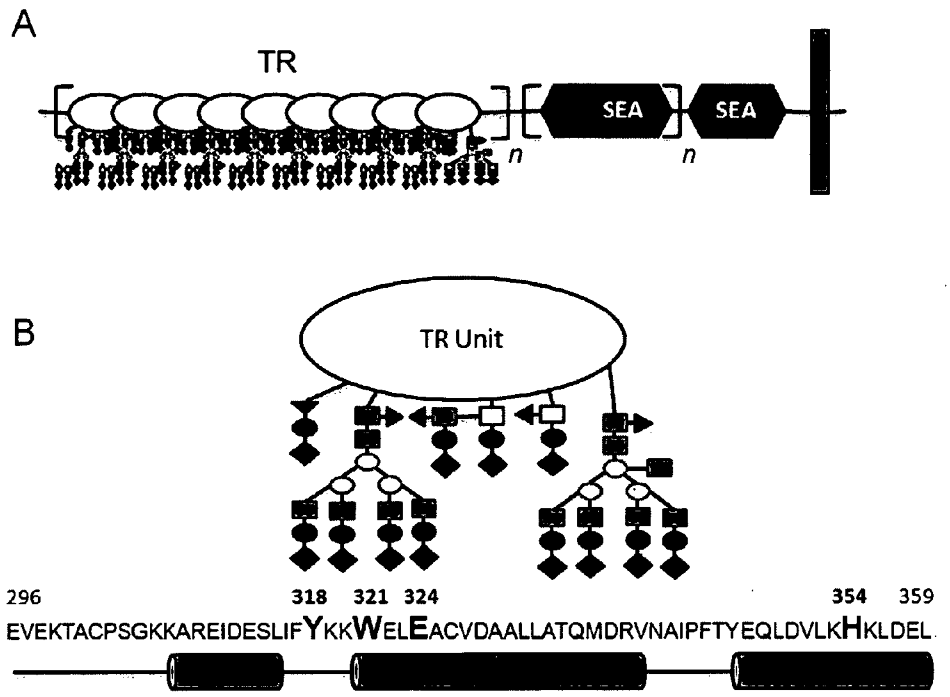
FIG. 10. Interaction of CA125 and mesothelin. A. CA125 is heavily glycosylated with both O-linked and N-linked oligosaccharides. The peptide backbone of CA125 is composed of the N-terminal region, extensive Ser/Thr/Pro-rich TR containing 165 amino acids each with both N- and O-glycosylations, a SEA domain with high levels of O-glycosylation and a C-terminal region with a short cytoplasmic tail. Previous studies have shown that the N-glycan (Gubbels, et al., (2006) *Mol. Cancer* 5, 50) in the TR region (Scholler, et al., (2007) *Cancer Lett.* 247, 130-136) is required for the binding of CA125 to mesothelin. B. The secondary structure of mesothelin 296-359 (SEQ ID NO:3) was evaluated by the algorithms PROF and APSSP2. The N-glycan moiety of CA125 repeat units binds to CA125-binding domain (Region IAB), likely the helical structures around Tyr-318 at the N terminal of cell surface mesothelin. Line: coil. Tube: helix.

Since a three-dimensional structure of mesothelin is currently not available, the secondary structure was evaluated by the algorithms PROF (on the worldwide web at predictprotein.org) and APSSP2 (on the worldwide web at imtech.res.in/raghava/apssp2). The CA125-binding domain is primarily composed of helix-turn-helix repeats (FIG. 10). Interestingly, Tyr-318 whose alanine replacement significantly reduces the CA125 binding is located at the coil between two helical secondary structures. The tyrosine seems a critical residue which either directly binds the N-glycan on CA125 or indirectly plays an important role by maintaining a conformation required for CA125 binding. The partial loss of CA125 binding activities of the W321A and E324A mutants may indicate that other residues near 318 are also involved. The fact that Region IB alone had only a modest CA125-binding activity (~10%) indicates that the CA125-binding domain requires residues in Region IA for its full activity.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A mesothelin fragment no longer than 95 amino acids and comprising the amino acid sequence of SEQ ID NO:2, wherein the fragment specifically binds to CA125.

2. The mesothelin fragment of claim 1, which consists of the amino acid sequence of SEQ ID NO:2.

3. The mesothelin fragment of claim 1, which consists of the amino acid sequence of residues 296-359 of SEQ ID NO:1.

4. A fusion protein consisting of the mesothelin fragment of claim 1 and one or more additional polypeptide not from mesothelin.

5. The fusion protein of claim 4, wherein the one or more additional polypeptide is selected from the group consisting of an Fc portion of an antibody, a cytokine, a chemokine, a carrier protein, a cytotoxin and an enzyme.

6. The fusion protein of claim 4, wherein the one or more additional polypeptide is an Fc portion of an antibody.

7. A composition comprising the mesothelin fragment of claim 1 or the fusion protein of claim 4 and a pharmaceutically acceptable excipient.

8. The composition of claim 7, further comprising an adjuvant.

9. A method of inhibiting CA125/mesothelin-dependent cell attachment comprising contacting a cell expressing CA125 with the mesothelin fragment of claim 1 or the fusion protein of claim 4.

10. The method of claim 9, wherein the mesothelin fragment consists of the amino acid sequence of SEQ ID NO:2.

11. The method of claim 9, wherein the mesothelin fragment consists of the amino acid sequence of residues 296-359 of SEQ ID NO:1.

12. The method of claim 9, comprising contacting the cell expressing CA125 with the fusion protein of claim 4.

13. The method of claim 12, wherein the one or more additional polypeptide is selected from the group consisting of an Fc portion of an antibody, a cytokine, a chemokine, a carrier protein, a cytotoxin and an enzyme.

14. The method of claim 12, wherein the one or more additional polypeptide is an Fc portion of an antibody.

15. The method of claim 9, wherein the contacting step is performed in vitro.

16. The method of claim 9, wherein the contacting step is performed in vivo.

17. The method of claim 16, wherein the mesothelin fragment is administered intraperitoneally or intratumorally.

18. The method of claim 16, wherein the mesothelin fragment is administered intradermally or subcutaneously.

19. The method of claim 16, further comprising administration of an adjuvant.

20. A method of inhibiting a cancer mediated by CA125/mesothelin-dependent cell attachment comprising contacting a cell expressing CA125 with the mesothelin fragment of claim 1 or the fusion protein of claim 4.

21. The method of claim 20, wherein the mesothelin fragment consists of the amino acid sequence of SEQ ID NO:2.

22. The method of claim 20, wherein the mesothelin fragment consists of the amino acid sequence of residues 296-359 of SEQ ID NO:1.

23. The method of claim 20, comprising contacting the cell expression CA125 with the fusion protein of claim 4.

24. The method of claim 23, wherein the one or more additional polypeptide is selected from the group consisting of an Fc portion of an antibody, a cytokine, a chemokine, a carrier protein, a cytotoxin and an enzyme.

25. The method of claim 23, wherein the one or more additional polypeptide is an Fc portion of an antibody.

26. The method of claim 20, wherein the cancer is selected from the group consisting of ovarian cancer, mesothelioma, non-small cell lung cancer, lung adenocarcinoma and pancreatic cancer.

27. The method of claim 20, wherein the mesothelin fragment is administered under a regime such that the mesothelin fragment directly binds to CA125, thereby inhibiting CA125/mesothelin-dependent cell attachment.

* * * * *